United States Patent
Braithwaite et al.

(10) Patent No.: US 7,048,963 B2
(45) Date of Patent: May 23, 2006

(54) LAYERED ALIGNED POLYMER STRUCTURES AND METHODS OF MAKING SAME

(75) Inventors: Gavin J. C. Braithwaite, Cambridge, MA (US); Jeffrey W. Ruberti, Lexington, MA (US)

(73) Assignee: Cambridge Polymers Group, Inc., Boston, MA (US)

( * ) Notice: Subject to any disclaimer, the term of this patent is extended or adjusted under 35 U.S.C. 154(b) by 0 days.

(21) Appl. No.: 10/306,825

(22) Filed: Nov. 27, 2002

(65) Prior Publication Data

US 2003/0141618 A1 Jul. 31, 2003

Related U.S. Application Data

(60) Provisional application No. 60/337,286, filed on Nov. 30, 2001.

(51) Int. Cl.
*B05D 3/12* (2006.01)

(52) U.S. Cl. .................. 427/2.24; 427/240; 427/425
(58) Field of Classification Search ............. 427/240, 427/425, 2.1, 2.24; 118/52, 320
See application file for complete search history.

(56) References Cited

U.S. PATENT DOCUMENTS 3,036,341 A * 5/1962 Taylor .................. 264/163
3,285,903 A * 11/1966 Taylor .................. 530/356
5,458,819 A 10/1995 Chirila et al. ............ 264/1.7

(Continued)

FOREIGN PATENT DOCUMENTS

EP 0454599 10/1991
WO WO 00/34442 6/2000
WO WO 01/92381 12/2001

OTHER PUBLICATIONS

Mertig, et al. "Scanning Force Microscopy and Geometric Analysis of Two–Dimensional Collagen Network Formation", 1997, Surface and Interface Analysis, vol. 25, pp. 514–521.*

Torbet et al, Biochemical Journal, 219(3), pp 1057–1059, 1984.*

Ghosh et al, Connective Tissue Research, 17(1), pp 33–41, 1988.*

Mingotaud et al, Journal of Physical Chemistry, 99(47), pp 17068–17070, 1995.*

Adachi, E., et al., "In Vitro Formation of Hybrid Fibrils of Type V Collagen and Type I Collagen Limited Growth of Type I Collagen into Thick Fibrils by Type V Collagen," Connective Tissue Research, vol. 14, 257–266, (1986).

(Continued)

*Primary Examiner*—Erma Cameron
(74) *Attorney, Agent, or Firm*—Heller Ehram LLP

(57) ABSTRACT

This invention includes a method of producing a thin, oriented layer of polymer material. The material is preferably produced by the method of introducing a shearing flow to a free surface in a predominantly monomeric solution of the self-assembling polymer sub-units, and inducing polymerization or growth of the monomer while in this shearing flow. The system for forming the oriented layer of material provides relative movement between a delivery system and the substrate on or over which the material is deposited. The rate of flow of the material from the delivery system and the relative velocity between the deposition surface and the material as it is delivered to the surface are controlled to properly orient the material at the desired thickness. These rates can be adjusted to vary the properties of the film in a controlled manner. Preferred embodiments include either angular or linear relative movement between the delivery system and the substrate.

73 Claims, 18 Drawing Sheets

U.S. PATENT DOCUMENTS

| | | | | |
|---|---|---|---|---|
| 5,733,337 | A | 3/1998 | Carr, Jr. et al. | 623/11 |
| 5,756,350 | A | 5/1998 | Lee et al. | 435/325 |
| 5,962,136 | A | 10/1999 | Dewez et al. | 428/410 |
| RE36,370 | E | 11/1999 | Li | 424/443 |
| 6,005,160 | A | 12/1999 | Hsiue et al. | 623/11 |
| 6,057,137 | A * | 5/2000 | Tranquillo et al. | 435/174 |
| 6,083,522 | A | 7/2000 | Chu et al. | 424/423 |
| 6,179,872 | B1 | 1/2001 | Bell et al. | 623/11.11 |
| 6,280,474 | B1 | 8/2001 | Cassidy et al. | 623/16.11 |
| 6,303,296 | B1 | 10/2001 | Bensimon et al. | 435/6 |
| 6,361,560 | B1 | 3/2002 | Nigam | 623/5.14 |
| 6,391,333 | B1 * | 5/2002 | Li et al. | 424/443 |
| 6,423,093 | B1 | 7/2002 | Hicks et al. | 623/5.11 |
| 6,471,958 | B1 | 10/2002 | Dimitrijevich et al. | 424/93.7 |
| 2003/0141618 | A1 | 7/2003 | Braithwaite et al. | 264/40.7 |
| 2003/0143335 | A1 * | 7/2003 | Qiu et al. | 427/430.1 |

OTHER PUBLICATIONS

Agarwal, U.S., et al., "Shear Flow Induced Orientation Development during Homogeneous Solution Polymerization of Rigid Rodlike Molecules," Macromolecules, 26, No. 15, 3960–3965, (1993).

Anna, S. L., et al., "Formation of Dispersions Using 'Flow–Focusing' in Microchannels," 1–10, (Aug. 8, 2002).

Bessea, L., et al., "Production of ordered collagen matrices for three–dimensional cell culture," Biomaterials, 23(1), 27–36, (Jan. 2000) (Abstract).

Birk, D. E., et al., "Collagen fibrillogenesis in vitro: interaction of types I and V collagen regulates fibril diameter," Journal of Cell Science, 95, 649–657, (1990).

Brown, C. T., et al., "Extraction and purification of decorin from corneal stroma retain structure and biological activity," Protein Express and Purification, 25, 389–399, (2002).

Chang, J. E., et al., "Air–interface condition promotes the formation of tight cornea epithelial cell layers for drug transport studies," Pharm. Res, 17(6):670–676, (Jun. 2000) (Abstract).

Emslie, A. G., et al. "Flow of a Viscous Liquid on a Rotating Disk," Journal of Applied Physics, vol. 29, No. 5, 858–862, (May 1958).

Engelmann, K., et al. "Transplantation of adult human or porcine corneal endothelial cells onto human recipients in vitro., Part I: Cell culturing and transplantation procedure," Cornea, 18(2): 199–206, (Mar. 1999) (Abstract).

Fleischmajer, R., et al., "Biology, Chemistry, and Pathology of Collagen," Annals of the New York Academy of Sciences, vol. 460, (Dec. 30, 1985) (Index).

Germain, L., et al., "Can We Produce a Human Corneal Equivalent by Tissue Engineering?," Progress in Retinal and Eye Research, vol. 19, No. 5, 497–527, (2000).

Giordano, N. and Cheng, J–T, "Microfluid mechanics: progress and opportunities," J. Phy.: Condens. Matter 13 (Apr. 16, 2001) R271–R295.

Griffith, M., et al., "Functional Human Corneal Equivalents Constructed from Cell Lines," Science, 286: 2169–2172, (Dec. 10, 1999).

Guido, S., et al., "A methodology for the systematic and quantitative study of cell contact guidance in oriented collagen gels," Journal of Cell Science, 105, 317–331, (1993).

Kadler, K. E., et al., "Assembly of Type I Collagen Fibrils de Novo," The Journal of Biological Chemistry, vol. 263, No. 21, 10517–10523 (Jul. 25, 1988).

Kadler, K. E., et al., "Collagen fabril formation" Biochem., J., 316, 1–11, (1996).

Maurice, D. M., et al., "The fate of scleral grafts in the cornea," Cornea, 15(2): 204–9, (Mar. 1996) (Abstract).

Parkinson, J., et al., "Self–assembly of rodlike particles in two dimensions: A simple model for collagen fibrillogenesis," Physical Review E, vol. 50, No. 4, 2963–2966, (Oct. 1994).

Pins G. D., et al., "Microfabrication of an analog of the basal lamina: biocompatible membranes with complex topographies," the FASEB Journal, vol. 14, 593–602, (Mar. 2000).

Schreckenbach, A., "Macroscopic structures in liquid crystal systems prepared with spin coating," Polymer, vol. 38 No. 12, 3069–3083, (1997).

Schwab, I., et al., "Bioengineered Corneas—The Promise and the Challenge," The New England Journal of Medicine, vol. 343:136–138, No. 2., (Jul. 13, 2000) (Editorial).

Scott, D. M., et al., "Investigation of the Attachment of Bovine Corneal Endothelial Cells to Collagens and Other Components of the Subendothelium," Exp Cell Res 144, 472–478, (1983).

Tsai, R., et al. "Reconstruction of Damaged Corneas by Transplantation of Autologous Limbal Epithelial Cells," The New England Journal of Medicine, vol. 343, No. 2, 86–93, (Jul. 13, 2000).

Varani, J., et al., "Modulation of adhesive properties of DEAE–dextran with laminin," Journal of Biomedical Materials Research, vol. 29, 993–997, (1995).

Karle, Isabella L., et al., "Crystal Structure of a Hydrophobic 19–residue Peptide Helix Containing Three Centrally Located D Amino Acids,", Proc. Natl. Acad. Sci., vol. 100, No. 24, Nov. 25, 2003, pp. 13946–13951.

Hartgerink, Jeffrey D., et al., "Peptide–amphiphile Nanofibers: A Versatile Scaffold for the Preparation of Self–Assembling Materials", Proc. Natl. Acad. Sci., vol. 99, No. 8, Apr. 16, 2002, pp. 5133–5138.

Orudjev, E., et al., "Segmented Nanofibers of Spider Dragline Silk: Atomic Force Microscopy and Single–Molecule Force Spectroscopy", Proc. Natl. Acad. Sci., vol. 99, Supple. 2, Apr. 30, 2002, pp. 6460–6465.

Fey–Lamprecht, F., et al., "Development of Membranes for the Cultivation of Kidney Epithelial Cells", Biomaterials, vol. 21, 2000, pp. 183–192.

Holy, C.E., et al., "Bone Marrow Cell Colonization of, and Extracellular Matrix Expression on, Biodegradable Polymers", Cells and Materials, vol. 7, No. 3, 1997, pp. 223–234.

Ruberti, J.W., et al., "Nanoscale Engineering of Type I Collagen Fibrils to Mimic the Multiple Layers of Aligned Lamellae in Cornea", ARVO annual meeting abstract search and program planner, abstract page No. 4218.

* cited by examiner

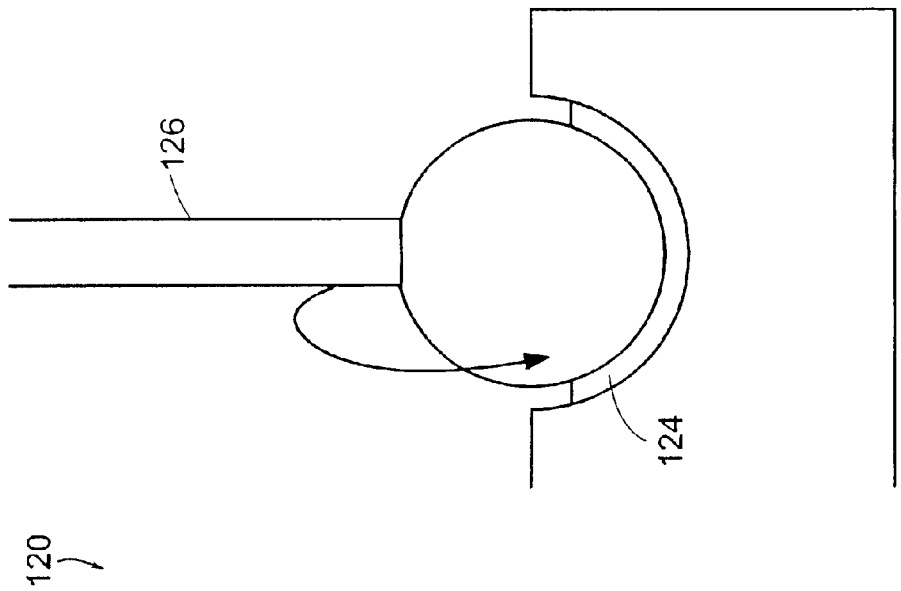
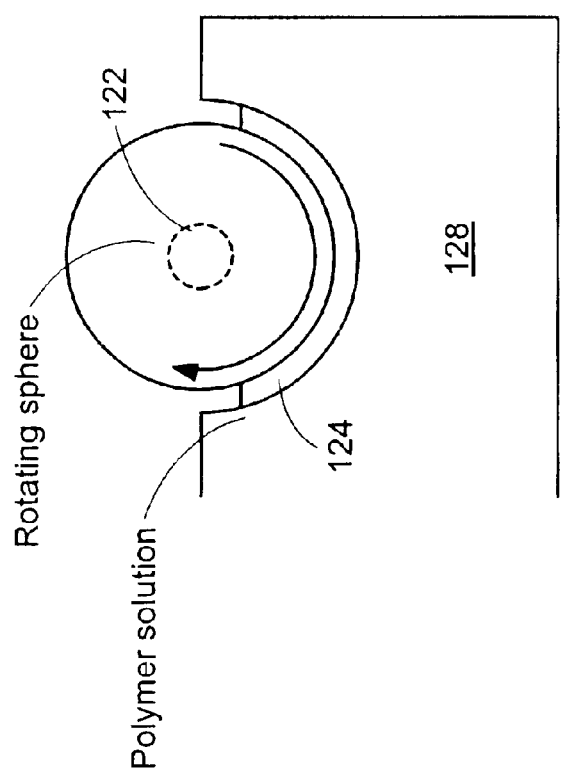
Figure 5B
Figure 5A

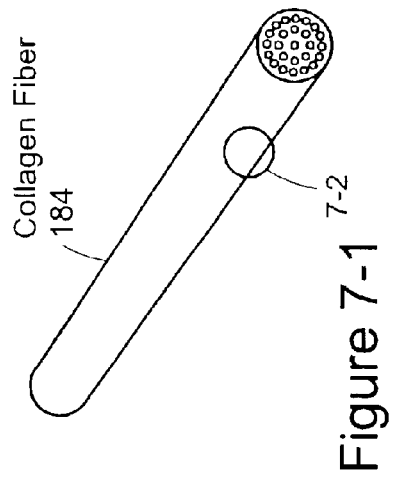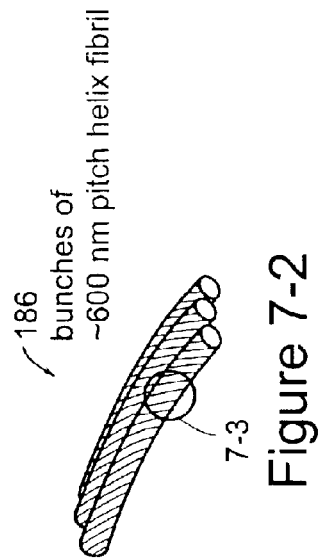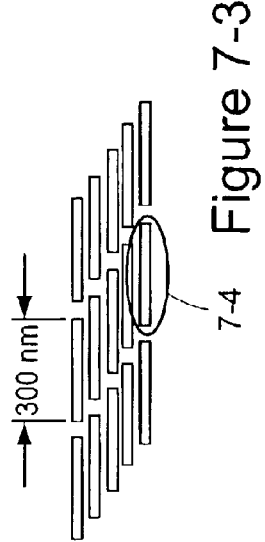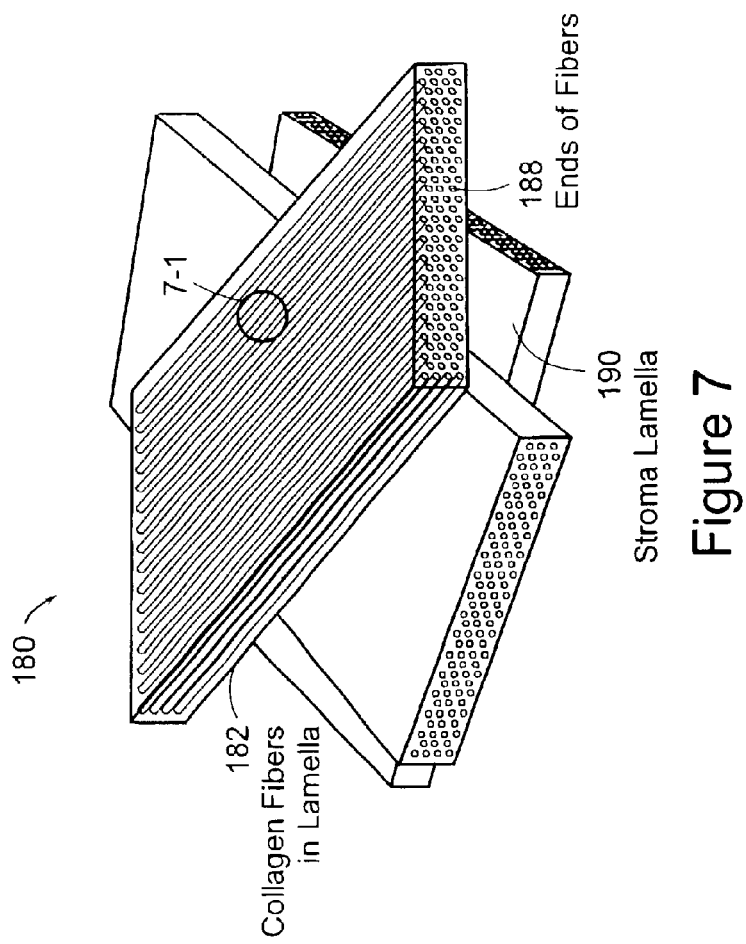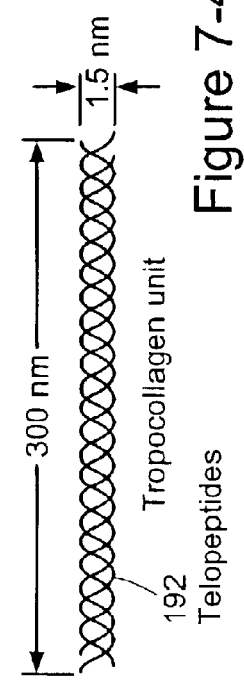

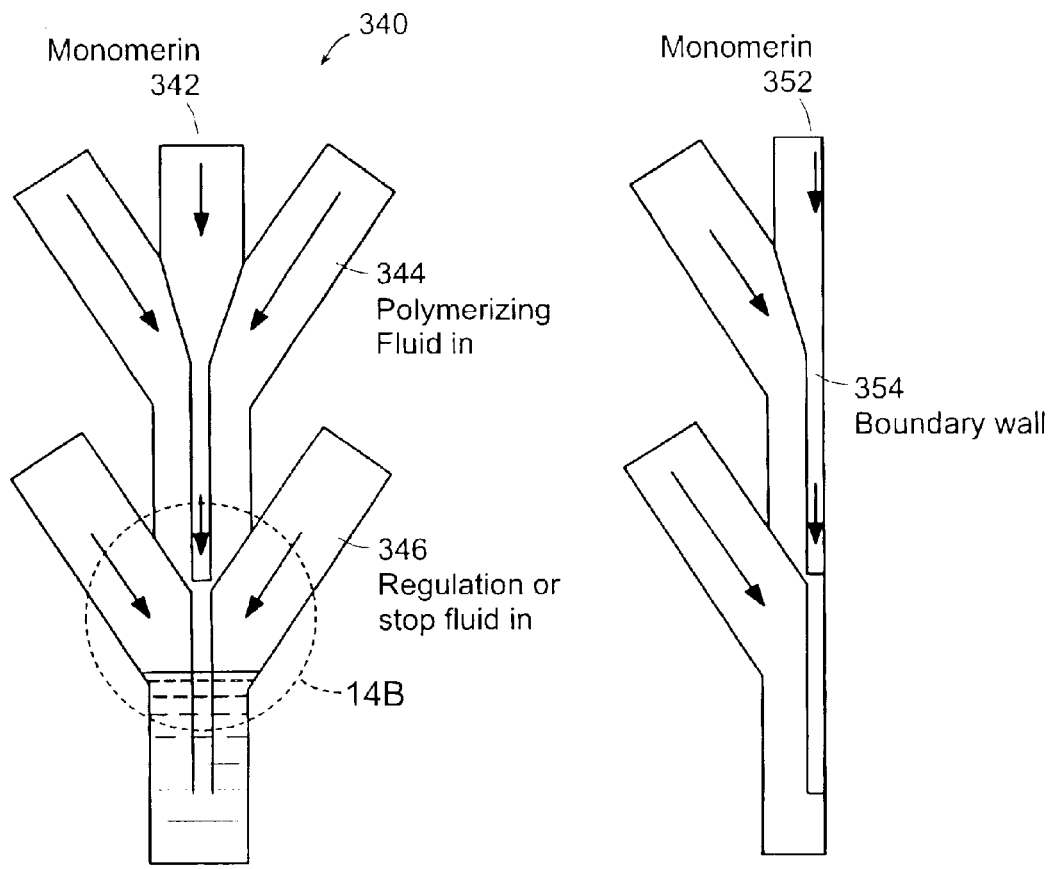
Figure 14A
Figure 14C
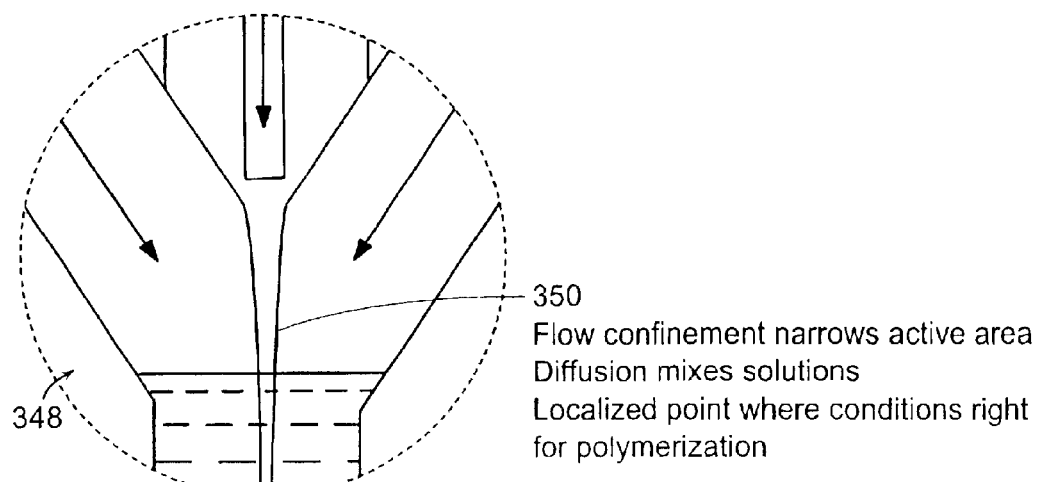
Figure 14B

LAYERED ALIGNED POLYMER STRUCTURES AND METHODS OF MAKING SAME

CROSS REFERENCES TO RELATED APPLICATIONS

This application claims the benefit of U.S. Provisional Application No. 60/337,286 filed on Nov. 30, 2001, the entire contents of which are incorporated herein by reference in its entirety.

BACKGROUND OF THE INVENTION

Accurate control of the orientation of polymeric structure in thin layers is desired to maximize their mechanical, chemical, and optical properties. While orientation can be performed through mechanical means, it is often more desirable to orient the structure during the polymerization process, particularly if the process involves polymerizing the system into a specific final shape, where further mechanical manipulation is unfeasible.

Biomedical components often require oriented structures. Tendons, for example, contain highly oriented collagen fibrils, and the spinal intervertebral disc is composed mainly of oriented crystalline collagen fibrils and amorphous hydrophilic proteoglycan. The prevalence of oriented collagen in the human body makes formation of highly oriented layers of this polymer a desired goal in modeling of tissue structure. Collagen is a biopolymer and protein, and found in the structure of tendons, skin, bones and blood vessels. Randomly oriented collagen materials are weak, and degrade quickly when exposed to mechanical stress. Soluble collagen is derived from animal tissue, and can be obtained in a monomeric form. The collagen monomer will polymerize, termed "fibrillogenesis," to form a gel-like structure. This process is achieved when the collagen is in a solution of specific pH, temperature, and ionic strength. The polymerization occurs as a self-assembly process, producing native-type collagen fibers. The fibers grow into a porous gel matrix.

The collagen molecule is a rod-like structure in the unaggregated state, composed of three peptide chains intertwined to form a triple helix. Improvements over randomly oriented gels in mechanical and optical properties can be realized if the aggregated molecules can be coerced into an oriented, or aligned, state. Cast films of collagen can form a randomly oriented gel structure, which lacks desired mechanical and optical properties. It is desirable to give a structured order for optical transparency in corneal replacements.

Collagen fiber orientation techniques have included mechanical deformation of already gelled matrices and laminar flow of a gelling matrix. These approaches yield gelled layers hundreds of microns thick.

SUMMARY OF THE INVENTION

This invention includes a method of producing a thin, oriented layer of polymer material. The material is preferably produced by the method of introducing a shearing flow to a free surface in a predominantly monomeric solution of the self-assembling polymer sub-units, and inducing polymerization or growth of the monomer while in this shearing flow. The system for forming the oriented layer of material provides relative movement between a delivery system and the substrate on or over which the material is deposited. The rate of flow of the material from the delivery system and the relative velocity between the deposition surface and the material as it is delivered to the surface are controlled to properly orient the material at the desired thickness. These rates can be adjusted to vary the properties of the film in a controlled manner. Preferred embodiments include either angular or linear relative movement between the delivery system and the substrate.

It should be noted that deposition of the polymer solution can occur on a substrate having curved or spherical surfaces to result in stress-free interlayer boundaries. This embodiment is enabling for corneal constructs.

In a preferred embodiment, the step of controlling the temperature, pH, solvent chemistry, and relative humidity during the polymerization process is performed on a local level.

The preferred embodiment of the present invention further comprises a layered construct composed of layers of sub-micron to 10 μm thick oriented polymeric films or fibers, with the principle direction of orientation alternating in each subsequent layer. A preferred embodiment of the invention uses this method to form synthetic biocompatible or biopolymeric materials such as implantible tissue material. These materials can be implanted as soft tissue replacement or for bone or joint replacement or repair.

In another preferred embodiment of the present invention, the method further includes inducing fibrillogenesis of the collagen while in this shearing flow. The method further includes controlling the collagen monomer concentration, temperature, solution properties and relative humidity of the fibrillogenesis process, producing collagen material having an oriented fibrillar structure in a sheet with a uniform, controllable thickness. The thickness can range from approximately 500 nm to 100 μm.

In accordance with another preferred embodiment, the method for producing a multi-layer construct can be used to form an artificial corneal construct. The collagen layers can be seeded with endothelial and epithelial cells, which generate a negative pressure field in the construct, and compress the construct to a thickness necessary for optical transparency.

A preferred embodiment includes a method of producing a thin film of oriented polymer structures, including the steps mixing a solution of collagen with phosphate buffered saline solution, adjusting the pH of the solution to 7.4±0.2, applying the solution at a controlled rate onto a substrate which generates a shearing flow, causing preferential orientation of the gelling collagen fibrils; and generating successive layers, each layer representing a portion of the component. The method layers have a uniform, controllable thickness ranging from sub-micron to 100 microns. The collagen is either type I or type V collagen. The principle orientation of the aligned fibrils in a single layer alternates in each successive layer. The angle between the principle orientation of each layer is approximately in the range of 0 to 180 degrees. The solution properties, including temperature, concentration and surfactant composition are controlled. The shear flow is generated by spinning the substrate at a controlled rate in a range of approximately 50 to 50,000 Hz.

In a preferred embodiment the shear flow is generated by drawing the substrate out of the collagen solution. Further, a preferred embodiment includes a system to align polymerizing polymer chains in a layer such that polymers are predominantly aligned parallel to each other, having an apparatus to generate shear flow, a plurality of sensors to monitor a plurality of parameters; and a processor to modulate a plurality of control parameters.

The foregoing and other features and advantages of the system and method for producing a multilayer construct of sub-micron to 10 micron thick layers of oriented collagen fibers will be apparent from the following more particular description of preferred embodiments of the system and method as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

FIGS. 5A–5C illustrate another preferred embodiment of an apparatus used to generate a matrix of orthogonally-aligned layers in accordance with the present invention.

FIGS. 7, 7-1, 7-2, 7-3 and 7-4 schematically illustrates collagen fibers in the lamellae of the stroma in accordance with a preferred embodiment of the present invention.

FIGS. 14A–14C schematically illustrate a nanofabrication system and a flow-focussing method to manufacture layered, aligned polymer structures in accordance with a preferred embodiment of the present invention.

DETAILED DESCRIPTION OF THE INVENTION

The systems and methods of the present invention relate to processes and resulting material, suitable for the guided production of the self-assembly of aligned polymers in layers, and structures having multiple, non-aligned layers. More particularly the systems and methods of the present invention relate to the production of self-assembled biocompatible non-aligned thin lamellae.

This invention will be better understood with reference to the following definitions:

"Self-assembly": a process by which a system spontaneously combines a number of smaller structural elements to form a large molecular or supramolecular complex. Self-assembly is the process by which many biological complexes form, such as DNA and collagen. This reaction sometimes requires that a threshold temperature, solution condition, or pH is reached before the spontaneous reaction occurs.

"Gel": a material that is crosslinked through bonds of sufficient strength that it cannot be dissolved in ambient conditions. The bonds can be covalent, ionic, physical, or other.

"Collagen": a self-assembling biopolymer produced by reacting monomeric collagen in a neutral pH, slightly ionic solution. Collagen is a structural building block in the body, and is found in the cornea, skin, bones, and blood vessels.

"Polymerization": the process by which monomer-sized molecules are assembled to form supramolecular structure. This process can occur through the formation of permanent chemical bonds, ionic bonds, or associative bonds. Fibrillogenesis is a form of polymerization in collagen.

"Polymer": any supramolecular structure comprised of repeating subunits. These structures can be naturally occurring, such as proteins, or man-made, such as polyolefins.

A preferred embodiment of the invention comprises a method to produce a highly oriented, thin film of self-assembled polymer. The method comprises the process of subjecting a solution of monomeric building blocks of the self-assembling polymer to a shearing flow. While under the influence of this shearing flow, the polymer self-assembles, forming oriented polymeric structure in a thin film from approximately 500 nm to 100 μm thick. The preferred embodiments of the present invention provide for several processes of generating this shearing flow, examples of which are described herein below. The systems and methods of the present invention also provide for a process of forming constructs with multiple layers of aligned polymer structures, each layer having a different principle direction of orientation. The preferred embodiments provide for a method of forming constructs in both biopolymers and synthetic polymers.

EXAMPLE 1

Figure 1:
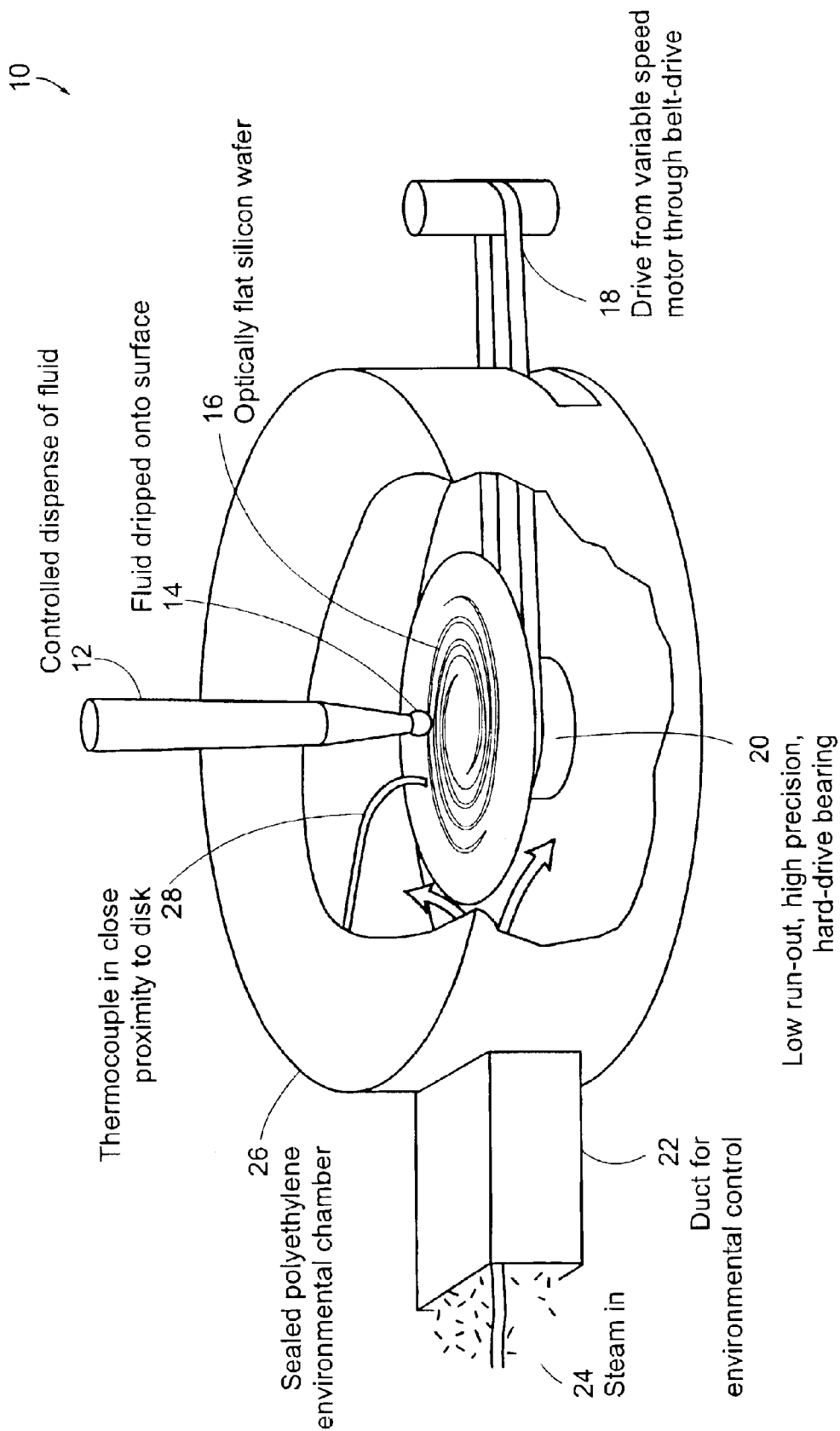
FIG. 1 illustrates a preferred embodiment of the apparatus used to generate a single layer of oriented self-assembled polymer molecules in accordance with the present invention.

As one example of a preferred embodiment of this present invention, a metal disk is used as a deposition substrate. The disk is mounted on a spin-coating-type apparatus. A chamber is built around the apparatus to control the temperature and the relative humidity. The disk can be spun at a specified rate. This embodiment is illustrated in FIG. 1.

Figure 2:
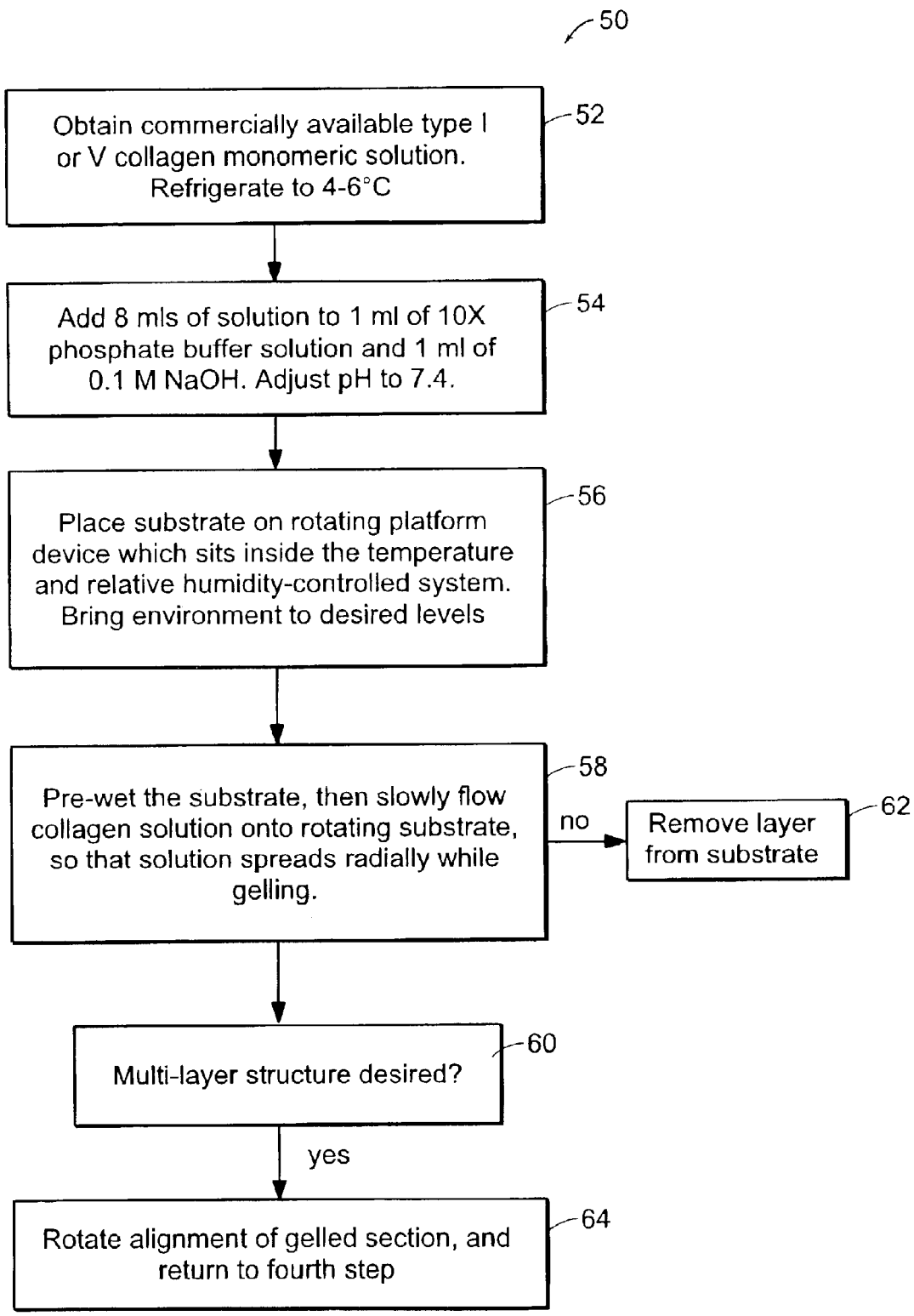
FIG. 2 illustrates a flow chart for producing aligned collagen fibers in accordance with a preferred embodiment of the present invention.
Figure 3A:
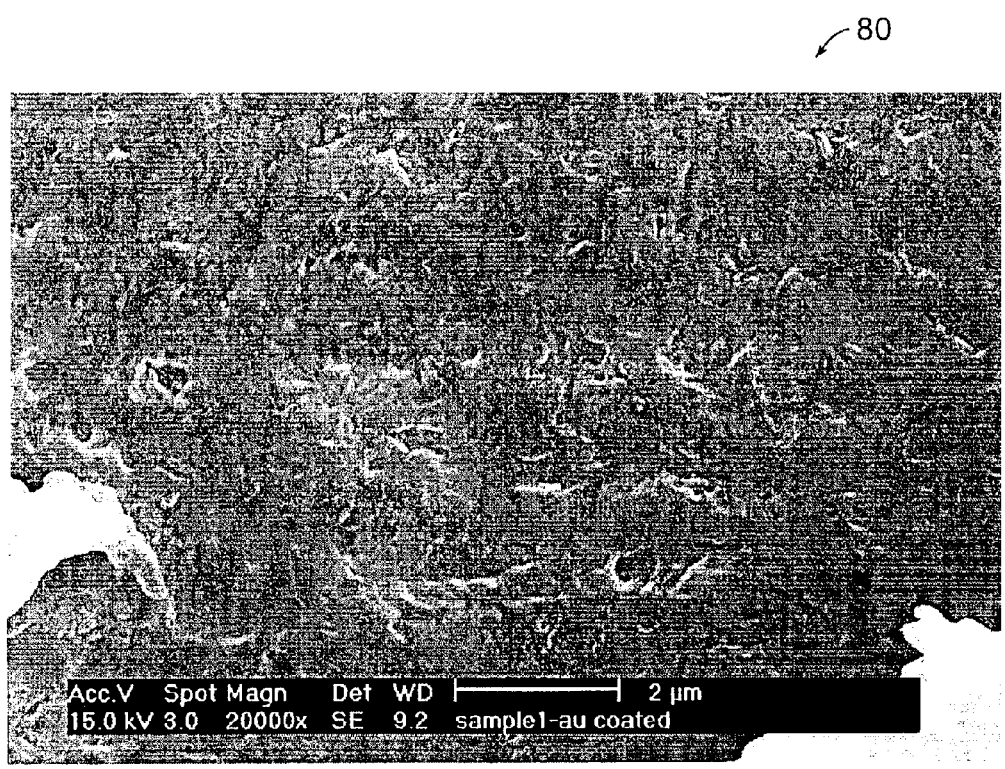
FIGS. 3A and 3B illustrate electron micrographs of collagen fibers prepared by a spin-coating method where FIG. 3A particularly illustrates random alignment of fibers and FIG. 3B illustrates fibers aligned in flow field in accordance with preferred embodiments of the present invention.
Figure 3B:
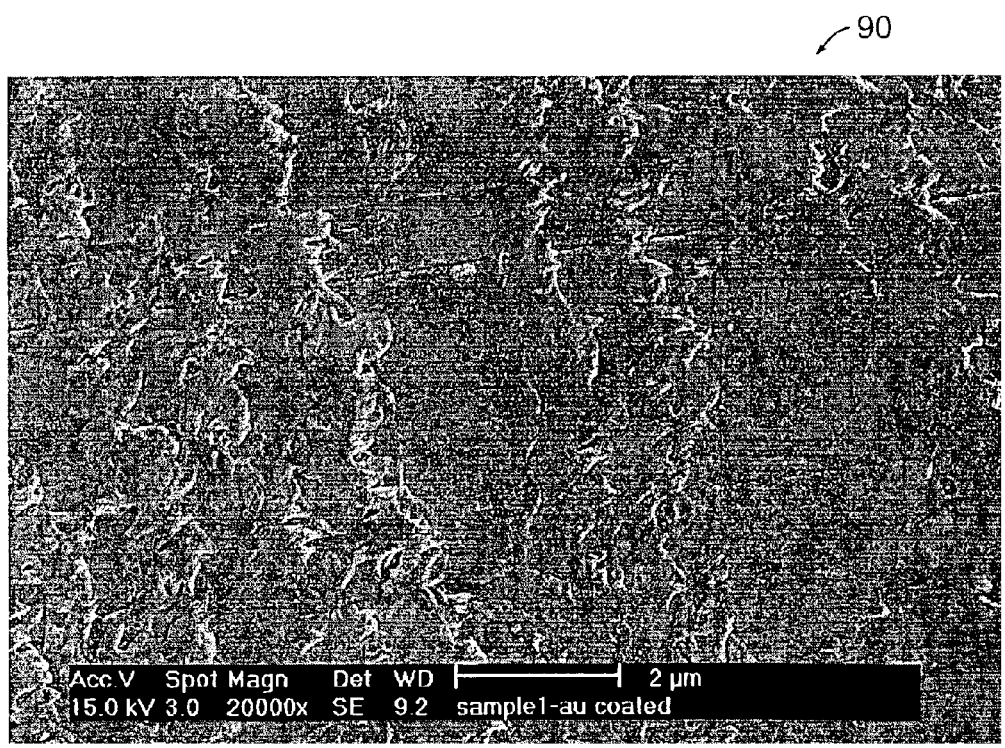

A solution of Vitrogen collagen is chilled to 4–6° C. Eight ml of the collagen solution is mixed with 1 ml of 10× phosphate-buffered saline solution (0.2 M $Na_2HPO_4$, 1.3M NaCl, pH=7.4) and 1 ml of 0.1M NaOH. The pH is adjusted to 7.4±0.2 by adding 0.1M HCl. The solution is warmed to the test temperature, then steadily dripped onto the rotating substrate 16. The collagen gels form a uniform sub-micron thick sheet. This process is described with respect to the flow chart illustrated in FIG. 2. Nematic stacks are prepared by cutting out sections of the radially-aligned collagen fiber sheets, and stacking them orthogonally by hand. Electron micrographs of randomly oriented collagen fibers and oriented collagen fibers in a single layer prepared by this method are shown in FIGS. 3A and 3B, respectively.

EXAMPLE 2

Figure 4A:
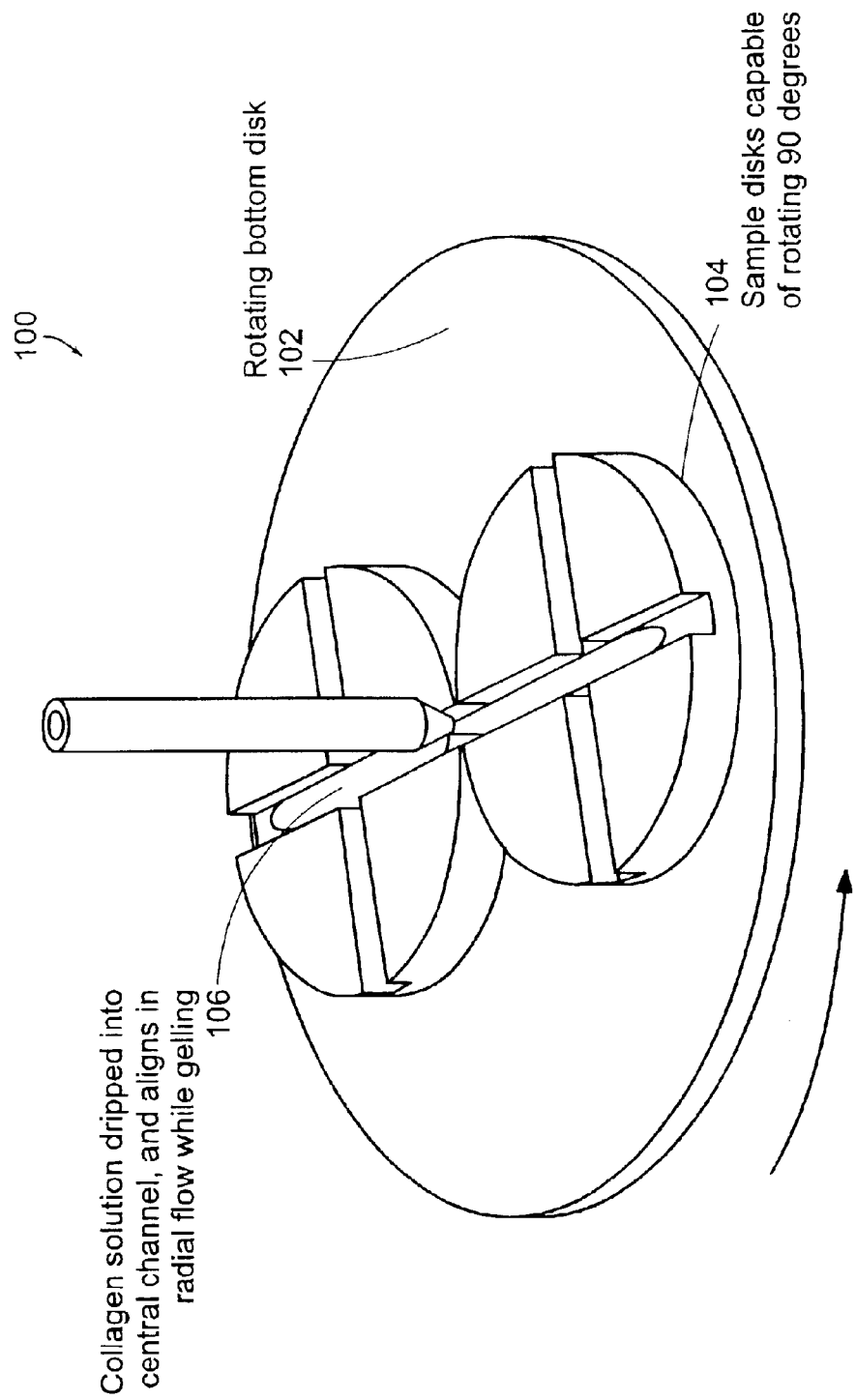
FIGS. 4A and 4B illustrate a preferred embodiment of the apparatus used to generate a matrix of orthogonally-aligned layers in accordance with the present invention.
Figure 4B:
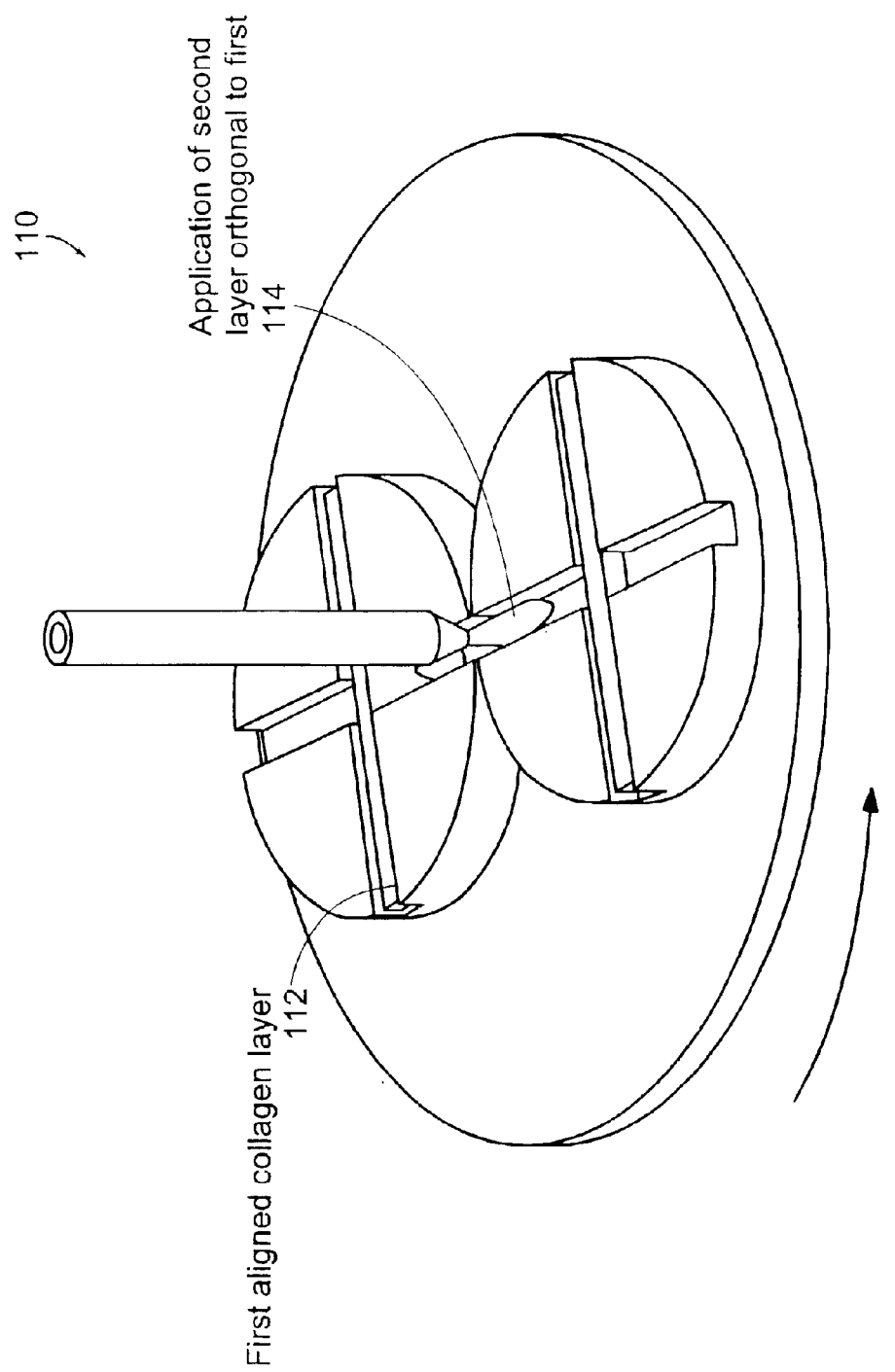

As a second example of a preferred embodiment of the present invention, sample disks 104 with T-slots cut into their surfaces are mounted on a disk 102 rotating at a specified rate as shown in FIGS. 4A and 4B. In accordance with a preferred embodiment of the present invention, the first layer of aligned associating fibrils is prepared by flowing the polymeric solution into channel of sample disks, which are on the rotating bottom disk. The centrifugal motion generates a shearing flow, which produces a thin layer and aids in aligning the growing associating polymers. The sample disks are then rotated 90 degrees, or to another specified angle, and the second layer is applied, which aligns with the specified angle relative to the first. A solution of Vitrogen collagen is chilled to 4–6° C. Eight ml of the collagen solution is mixed with 1 ml of 10×phosphate-buffered saline solution (0.2 M $Na_2HPO_4$, 1.3M NaCl, pH=7.4) and 1 ml of 0.1M NaOH. The pH is adjusted to 7.4±0.2 by adding 0.1M HCl. The solution is warmed to the test temperature, then steadily dripped onto the center of the rotating disk, so that the solution travels down the channels extending to the outer radius of the rotating disk. After the first layer has gelled into an oriented collagen film, the sample disks are rotated 90 degrees, and the second layer is applied, so that the orientation direction of the second layer is 90 degrees with respect to the first layer. This process is repeated many times to generate a matrix of orthogonally-oriented collagen fibril layers.

EXAMPLE 3

Figure 5C:
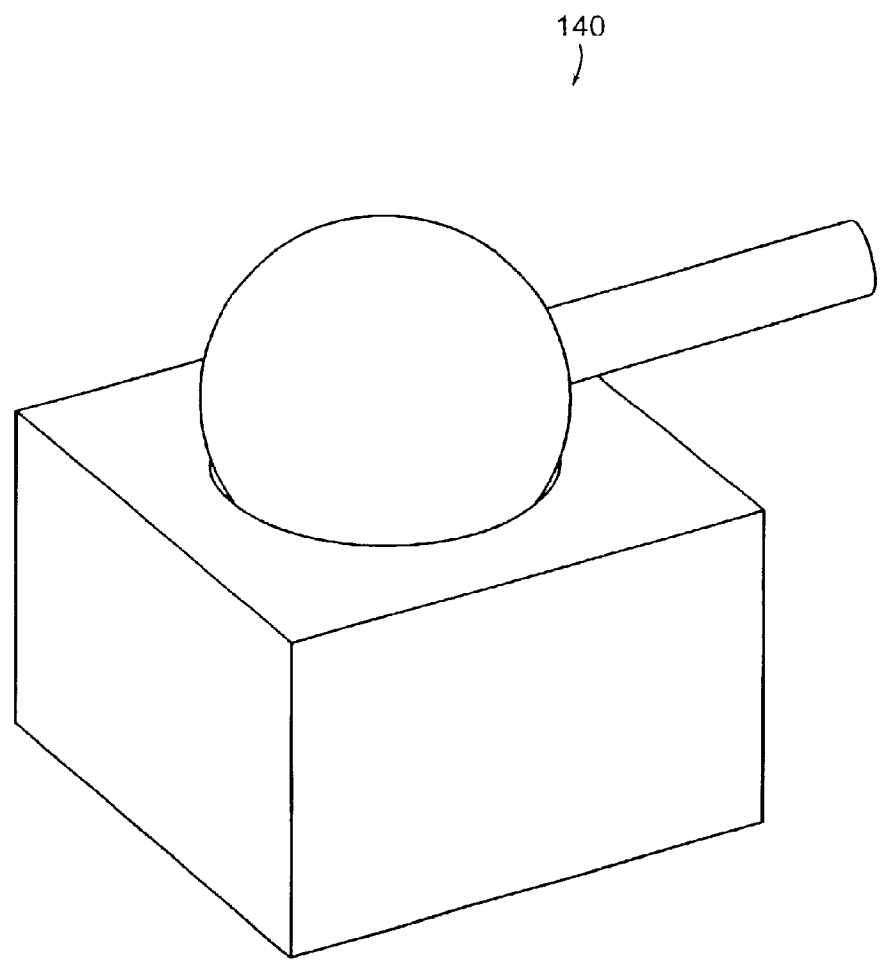

Another preferred embodiment of the present invention includes the monomer solution being placed in a temperature-controlled bowl as shown in FIGS. 5A–5C. In FIG. 5A, the polymer solution is subjected to a shearing flow by rotating the ball in one direction, or by oscillating in the same rotation plane. The polymer associates during this process. In FIG. 5B, the ball is rotated or oscillated in the orthogonal plane, to generate a layer of associated polymers orthogonal to the first layer. In FIG. 5C a three-dimensional (3D) rendering of the method is illustrated. A ball 122 with a diameter a few microns smaller than the bowl 128 diameter is placed in the bowl. A shaft 126 attached to the ball rotates the ball first in one direction, generating a shearing flow, during which time the monomer polymerizes. After a designated gelation period, fresh monomer solution may be introduced to the bowl, and the ball is rotated in the orthogonal direction, creating a layer orthogonally-aligned to the first layer.

EXAMPLE 4

As another preferred embodiment of the material described in this invention, epithelial cells and endothelial cell layers are established in the structure generated in either of the first three examples with collagen to develop a corneal construct. This construct produces a cornea that is similar physiologically, ultrastructurally and biochemically to normal mammalian corneas. The construct is suitable as a physiological or biomechanical model, and may find utility as a material for transplant into human subjects.

EXAMPLE 5

As another embodiment of the material described in this invention, highly oriented collagen layers prepared as described herein can be bundled to form the annulus fibrosus found in the spinal intervertebral disk. This disk acts primarily as a weight-bearing and flexible joint. The load bearing capability and flexibility in selected directions is achieved by the combination of the annulus fibrosus and nucleus pulposus. Annulus fibrosus is a layered structure that is rigid in the radial direction but deformable in the axial direction and by torque. This structure has alternating layers of oriented collagen fibrils, similar to that described in the cornea. Each layer has its collagen fibrils wound at an angle, and subsequent layers have an alternate orientation. Such a structure helps to achieved a maximum resistance to radial stress, while allowing a deformation in torque and bending.

EXAMPLE 6

Figure 6A:
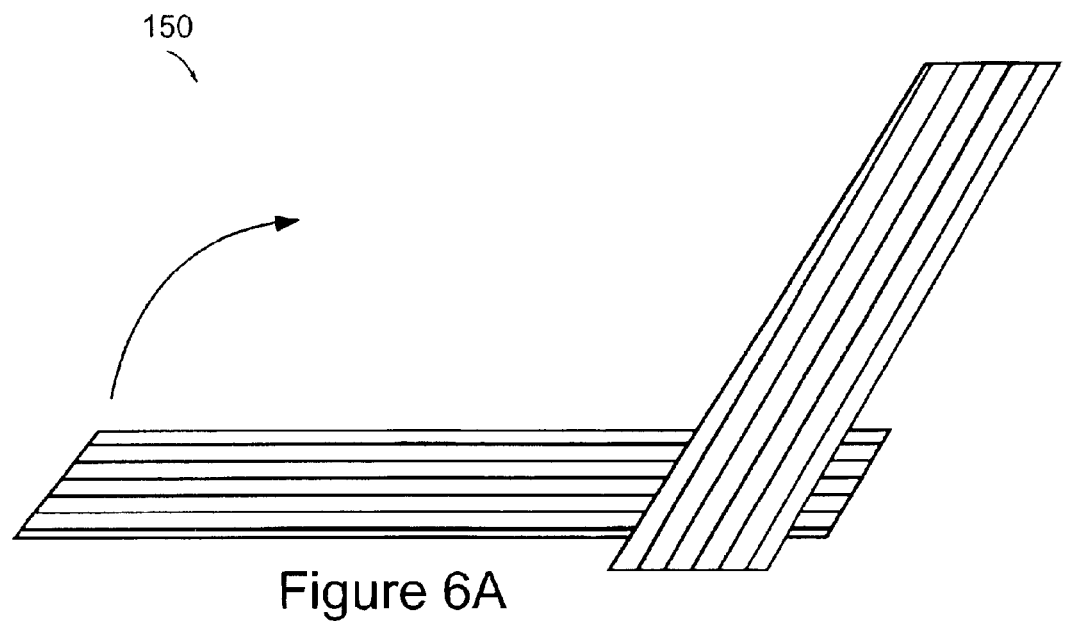
FIGS. 6A–6C illustrate schematically a folding method to generate a multilayer structure with orthogonally-aligned layers in accordance with a preferred embodiment of the present invention.
Figure 6B:
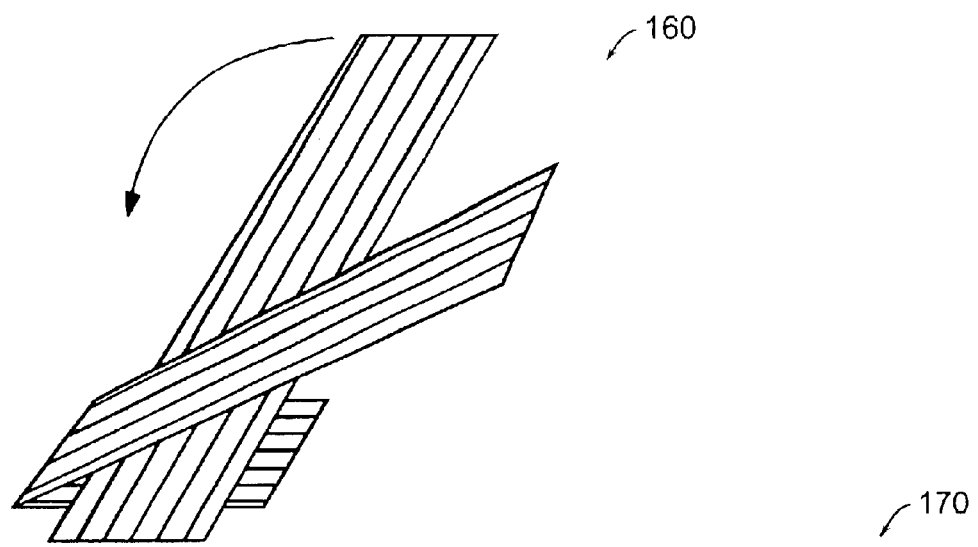
Figure 6C:
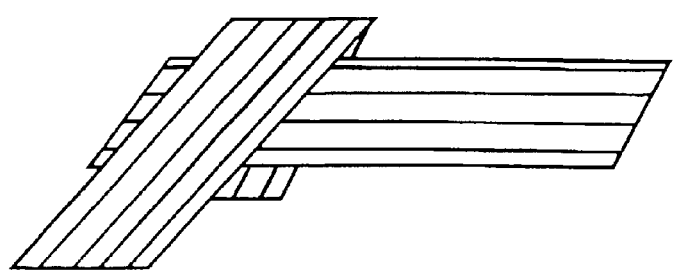

As another preferred embodiment of this invention, single layers of aligned polymer structure are generated with the techniques and methods discussed herein. The layers are folded as shown in FIGS. 6A–6C, to generate successively crossed layers of aligned polymer fibrils or other superstructure.

The extracellular matrix of the mature intact cornea comprises an extremely varied yet highly structured array of collagens, proteoglycans, glycoproteins and soluble macromolecules.

Current attempts to generate a biomimetic corneal construct have yielded corneas that behave similarly to in vivo corneas with respect to the function of the cellular layers. However, these corneal constructs have severe limitations with regard to the structure of the stromal extracellular matrix (ECM), which was constructed to ensure biocompatibility, nominal transmittance and the ability to promote adherence of the superficial cell layers and little more. It appears that previous investigators focused on the cellular layers but lost sight of the importance of the stroma itself. The three major functions of the cornea: protection, refraction and transmission, are performed primarily by the stromal ECM, the structure of which is optimally designed to accomplish these objectives. Thus, the cellular layers serve only to maintain and defend the stroma, which provides the principle functions of the cornea:

Strength. The major structural collagen of the stroma (type I collagen) is arranged in 300 to 500 lamellae of parallel, non-crosslinked fibrils. The lamellae are stacked in the anterior posterior (AP) direction and the fibrils of adjacent lamellae are nearly perpendicular to each other. Free ends of the fibrils have not been discerned in the cornea, which suggests that they run uninterrupted from limbus-to-limbus. This "plywood" arrangement of the lamellae gives the cornea remarkable strength tangential to the surface. Randomly crosslinked collagen networks of similar thickness (used in current constructs) cannot provide similar yield strength.

Refraction. The ability of the fibrils to slide relative to each other with ease allows the natural cornea to distribute the load imposed by the intraocular pressure (IOP) uniformly. This enables the anterior surface of the eye to form a nearly perfectly spherical shape for refraction. Stromas comprising randomly cross-linked collagen are likely to form imperfect surfaces for refraction upon inflation to normal IOP. This is due to the complex stress fields that would be produced when they are loaded.

Transmission of light. The uniform diameter of natural corneal fibrils and their short-range ordering allows light to pass through virtually unimpeded. Randomly crosslinked collagen networks, though nominally transparent, cannot produce the same quality optical properties. The process described in the embodiments of this invention can produce orthogonally stacked arrays of aligned type I/type V collagen fibrils. The general biomechanical and optical properties of such a construct should be similar to native corneal stroma.

The difficulties in forming a fully complete, functional, corneal stroma, constructed de novo, by artificial means have led some to indicate that it may not be a viable given the technology available today. However, it is not likely to be necessary to complete the construction of the stroma purely by mechano/chemical manipulation of biochemical components in the laboratory. A partially completed primary corneal stroma comprising orthogonal layers of aligned type I/type V heterotypic collagen fibers can suffice as a suitable scaffolding or starting point, as it does during embryogenesis. In support of this approach, it is known that following full-thickness trephination wounds in rabbit corneas, the healing response is capable of transforming the initially opaque fibrous plug to tissue that is similar to normal corneal stroma. The initially opaque scars comprise large interfibrillar spaces, unusually large chondroitin sulfate (CS) proteoglycans, hyaluronic acid and no detectable keratan sulfate proteoglycan. After one year of healing and remodeling, normal interfibrillar spacing, size and distribution of proteoglycans is restored. This mechanism works even if tissue of similar biochemistry, but not structure is implanted into the cornea. It has been found that the corneal healing response has the capacity to partially resolve collagen fibril structure even when scleral tissue is used to repair corneal wounds (Winkelman 1951 Am J Ophthalmol; Kurz 1953 Cs Oftal; Maurice and Singh Cornea 1996) incorporated herein by reference in its entirety. The present invention takes advantage of the natural healing response and remodeling ability of the corneal stroma. A stromal scaffolding remodeled by the corneal wound healing response, can be implanted. However, implanting a biomimetic stroma that is not sufficiently strong, transparent, or smooth at the outset is not viable. The artificial stroma, at the outset, must preserve the optical qualities of the cornea during the remodeling period. Current corneal constructs, which employ randomly cross-linked type 1 collagen fibrils, cannot meet this requirement.

The closer the tissue or scaffolding to be remodeled mimics native stroma, the less time it takes to fully resolve the structure and fully incorporate the graft. Further, if the initial scaffolding is capable of performing the three major functions of the stroma (protection, refraction and transmission), remodeling in vivo may proceed while vision remains clinically acceptable.

Thus, from investigations into the developmental biology of the chicken, it has been learned that corneal embryogenesis is an intricately orchestrated and complex phenomenon. Initially, from superficial epithelial cells derived from an offshoot of the developing brain, an orthogonally organized primary corneal stroma of type I collagen is secreted layer-by-layer. The extracellular matrix (ECM) of the mature intact cornea comprises an extremely varied yet highly structured array of collagens, proteoglycans, glycoproteins and soluble macromolecules.

The three major functions of the cornea: protection, refraction and transmission, are performed primarily by the stromal ECM, the structure of which is optimal to accomplish these objectives. Thus, the cellular layers serve only to maintain and defend the stroma. In addition, the major structural collagen of the stroma (type I collagen) is arranged in approximately 300 lamellae of parallel, non-crosslinked fibrils. The lamellae are stacked in the anterior posterior (AP) direction and the fibrils of adjacent lamellae are nearly perpendicular to each other. Free ends of the fibrils have not been discerned in the cornea, which suggests that they run uninterrupted from limbus-to-limbus. This "plywood" arrangement of the lamellae gives the cornea remarkable strength in tension tangential to the surface. Randomly crosslinked collagen networks of similar thickness (used in current constructs) cannot provide similar yield strength.

The ability of the fibrils to slide relative to each other with ease, allows the natural cornea to distribute the load imposed by the intraocular pressure (IOP). This enables the anterior surface of the eye to form a nearly perfectly spherical shape for refraction. Stromas comprising randomly cross-linked collagen are likely to form imperfect surfaces for refraction upon inflation to normal IOP. When these random networks are loaded, complex stress fields are formed that result in inhomogeneous refraction and thus compromised optical qualities.

The uniform diameter of natural corneal fibrils and their short-range ordering allows light to pass through the cornea virtually unimpeded. Randomly crosslinked collagen networks, though nominally transparent, cannot produce the same quality optical properties because of the varying spacing in the random network.

With regard to biomimetic corneal constructs, recent attempts have been made to develop full corneal constructs de novo. These efforts have yielded corneas that behave similarly to in vivo corneas with respect to the function of the cellular layers. However, both of these corneal constructs have severe limitations with regard to the structure of the stromal ECM, which was constructed to ensure biocompatibility, adequate transmittance and the ability to promote adherence of the superficial cell layers and little more.

Completely artificial corneal replacements, such as the K-pro, have not met with widespread clinical success. Such devices are not yet qualified for use in clinical situations where a transplant would be considered even marginally effective because of the high potential for devastating complications and the need for continual high quality follow-up. Current incarnations of corneal constructs generated from biomimetic materials and live cell layers do not include physiologically, ultrastructurally or biochemically realistic stromas. In addition there have been a number of efforts towards the production of an artificial cornea which have not met with complete success.

With regard to effective scaffolding and wound healing response, a fully complete, functional, corneal stroma, constructed de novo, by artificial means may not be a viable approach given the technology available today. However, it is not likely to be necessary to complete the construction of the stroma purely by mechano/chemical manipulation of biochemical components in the laboratory. A partially completed primary corneal stroma comprising orthogonal layers of aligned type I/type V heterotypic collagen fibers might suffice as a suitable scaffolding or starting point, as it does during embryogenesis. Such a partial solution would be a marked improvement over current systems, allowing easy cell infiltration and critically, immediate functionality both optically and mechanically. In support of this approach, it is known that following full-thickness trephination wounds in rabbit corneas, the healing response is capable of transforming the initial opaque fibrous plug/scar to tissue that is similar to normal corneal stroma. The initially opaque scars comprise large interfibrillar spaces, unusually large chondroitin sulfate (CS) proteoglycans, hyaluronic acid and no detectable keratan sulfate proteoglycan. After one year of healing and remodeling, normal interfibrillar spacing, size and distribution of proteoglycans is restored. This mechanism works even if tissue of similar biochemistry, but not structure is implanted into the cornea. It has been found that the corneal healing response has the capacity to partially resolve collagen fibril structure even when scleral tissue is used to repair corneal wounds. This suggests that it might be possible to take advantage of the natural healing response and remodeling ability of the corneal stroma. Stromal scaffolding, which can be remodeled by the corneal wound healing response, can be implanted. However, implanting a biomimetic stroma that is not sufficiently strong, transparent, or smooth is not acceptable. The artificial stroma, at the outset, has to preserve the optical qualities of the cornea during the remodeling period. Current corneal constructs, which employ randomly cross-linked type I collagen fibrils, cannot meet this requirement.

FIGS. 7, 7-1, 7-2, 7-3 and 7-4 illustrates collagen fibers in the lamellae of the stroma in accordance with a preferred embodiment of the present invention. The behavior of associate rods (collagen) in solution is explored. Collagen fibrils are composed of triple-helix collagen macromolecules that are approximately 300 nm long and 1.5 nm in diameter. These segments are produced inside cells and are excreted as procollagen whereupon the ends are removed to form a macromolecule that naturally self-assembles. Although there is some debate over the exact mechanism of this self-assembly process, it is understood that the assembly of collagen macromolecules into fibrils is an entropy driven process. The most favorable structure is therefore a cylinder 184 which minimizes the surface area. This fibril assembly is very similar to other protein polymerizations. Each of these cylindrical bundles is composed of segments of associated molecules in the familiar 67 nm repeating structure. There is still some debate over the exact molecular process of association but it appears that the cylindrical bundles of segments end-associate whereby the terminating C-telopeptide 192 associates with the N-telopeptide on the adjacent chain. The telopeptides also influence the diameter of the fibril and the segment packing, but there are also probably influences from glycoseaminoglycans (GAGs), proteoglycans, solution temperature and concentration. All of these components can be controllable in a manufacturing process. Further, there is some evidence that the association is driven by a further hydrophobic effect between the telopeptides. These fibrils then associate to form fibers.

Thus with no other influence, a solution composed of collagen macromolecules (i.e. the basic triple helix unit) forms an isotropic random gel. However, with the correct driving force, these gels can be forced to grow in an aligned manner. Magnetism, drainage flows and confining effects have both been used successfully, but only with weak influence on the morphology of the resulting gels.

Orientation of a rigid-rod in a flow field is determined by the balance of hydrodynamic forces (aligning) and rotary Brownian motion (randomizing) which is described by the Peclet number $Pe=II_{2D}/D_r$, where $D_r$ is the Brownian diffusion coefficient and $II_{2D}$ is the convective diffusion coefficient. Simple estimates suggest that the flow field can orient the collagen monomers because of their size (Pe<I) but that in fact for the monomers the flow is very close to the transition ranges. However, as the monomers associate and the collagen fibrils grow, the aspect ratio increases and consequently the Peclet number increases rapidly as it is related to the cube of the length of the rod.

$$Pe = \frac{II_{2D}^{1/2}}{D_r} = \frac{\dot{\gamma}}{D_r} \qquad \text{Equation 1}$$

$$= \frac{8\pi\eta_s a^3 \dot{\gamma}}{3kT(\ln(2r_p) - 1/2)} \qquad \text{Equation 2}$$

for thin prolate spheroids ($r_p \gg 1$) in shear flow, wherein $$r_p = \frac{a}{b}$$

is the aspect ratio of spheroid (a is long dimension). At 300 K for rigid rods of length 300 nm and diameter 30 nm in a solvent of 1 mPa.s and at a shear rate of 600 s$^{-1}$ the Peclet number is 13.

In addition, the proximity of walls also act to orient the monomers in the plane of the wall. This influence is especially strong in the confined films which are only of an order of magnitude larger than the longest axis of the collagen monomers. Concentrated solutions of rigid non-interacting rods are known to behave in a liquid crystalline fashion, forming nematic structures where there is long range order in the direction of the long axis of the rod. In theory, the direction of this ordering is arbitrary but is usually generated by perturbations, such as the confining effect of a wall, or solvent flow. Although nematic structures built from non-interacting rods require a critical concentration to transition from an isotropic to a nematic phase. In the case of interacting rods, the situation is more complex, but the interactions can clearly influence the ability of the molecules to align. Once fibrils have begun to grow the flowing monomers passing across the substrate in the shear field naturally end attach since there is a pronounced anisotropy between side addition and end addition for interacting rods. In addition magnetic (or electric) fields are known to strongly align nematic liquid crystals and have been proven to influence the alignment of growing collagen gels.

With regard to the alignment of polymers, it is well known that flow aligns polymers. Both shear and extensional flows align polymers in different manners but in general if the flow is strong enough there is some form of alignment in the direction of the flow. Spin-coating, and other similar flows, such as film drainage and steady shear, have been observed to produce roughly oriented polymers from the melt, for rigid-rod molecules and for liquid crystals. Alignment in these systems is often however only local and is usually for systems where the macromolecules themselves are being aligned. The alignment of growing fibers or polymers is less well recognized a process.

It has also been observed that shear induces alignment in polymers during the polymerization process of rod-like molecules. However simple shear does not provide sufficient force to counter the random fluctuations of the chains, and their natural propensity move under Brownian motion. The preferred embodiments of the present invention use spin-coating methods to provide a flow regime suitable for initiation and growth of aligned collagen fibrils. The solution conditions can be modulated while the polymerization process is proceeding, and the naturally radial nature of the flow assists in maintaining the fiber separation and promotes growth from a central core area. In addition the spin-coating process provides a natural length scale that can be easily adjusted to control the layer thickness and rate of polymerization. Also, since it is known that the proximity of a surface influences the position of an adjacent molecule, the thin confinement layer promotes alignment in the most critical direction, parallel to the layers longest axis. Spin-coating has been used to produce thin homogeneous films for a number of years. In melts and liquid crystals this deposition process is known to align polymers. This method is extremely well understood for evaporating and non-evaporating solvents since it is used heavily commercially in silicon microfabrication processes and in the optics industry.

With regard to the alignment of collagen, examples of artificial alignment of collagen are relatively common in the literature, but rarely result in the highly aligned configuration that is required for a truly biomimetic system. Previously noted parameters such as gravity, shear, diffusion and other external forces can influence the morphology of the fibers, but in all cases the alignment is weak. Other observations include alignment of collagen-like self-assemblies using shear while cooling from a hot solution. All of these cases require relatively concentrated solutions which limit the control over the fiber morphology. In addition collagen has been aligned using the natural propensity of collagen monomers to self-assemble in concentrated solutions. However, this method allows no control of the fiber sizes and shapes. To provide the highly aligned morphology two things are critically required, a thin confinement layer, and a unidirectional flow. Spin-coating provides both requirements readily. Although spin-coating has been observed to generate alignment in thin films, these are usually from melts and in polymerized systems. It should be noted that alignment as traditionally detected for many of these systems, using Circular Dichroism, does not indicate alignment on the levels required by a corneal analog.

Figure 8A:
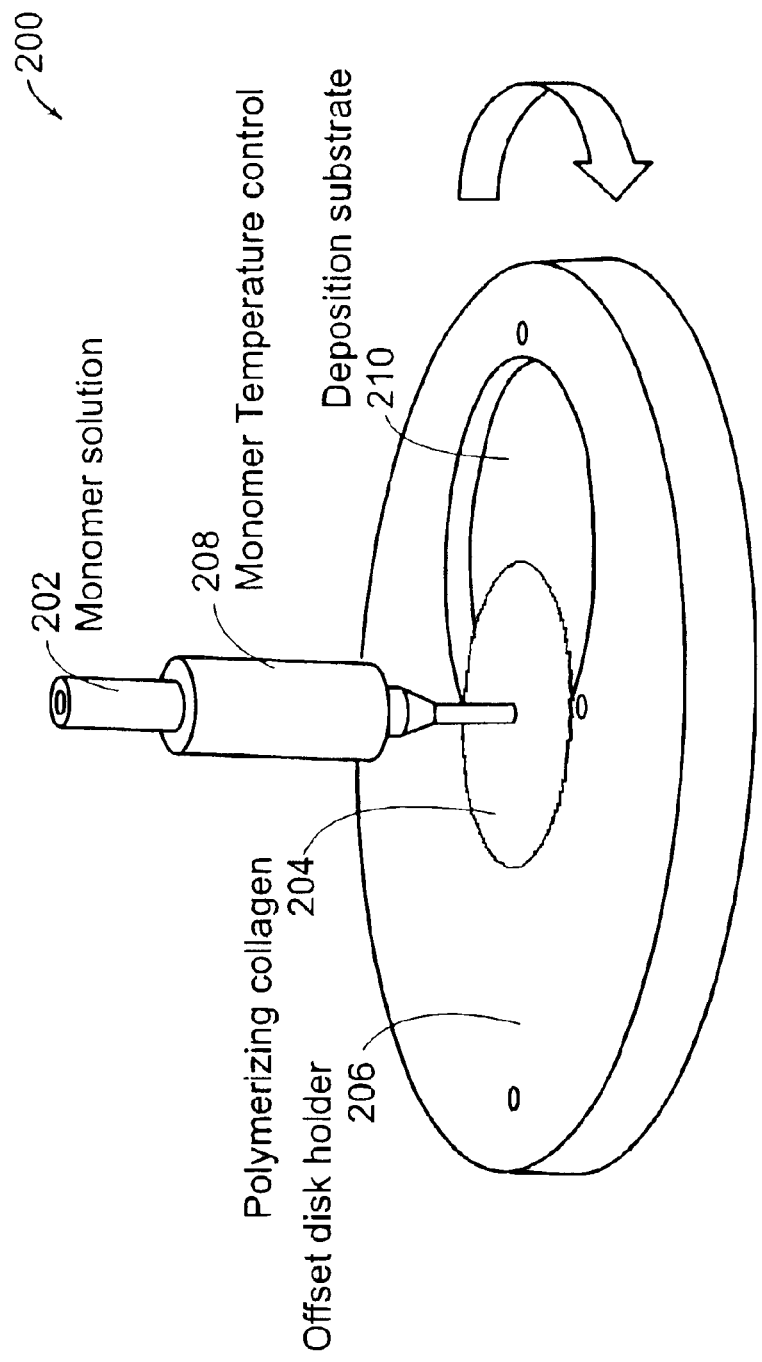
FIG. 8A illustrates an apparatus having an offset holder wherein a monomer solution is deposited onto the substrate at the center of the offset disk holder in accordance with a preferred embodiment of the present invention.
Figure 8B:
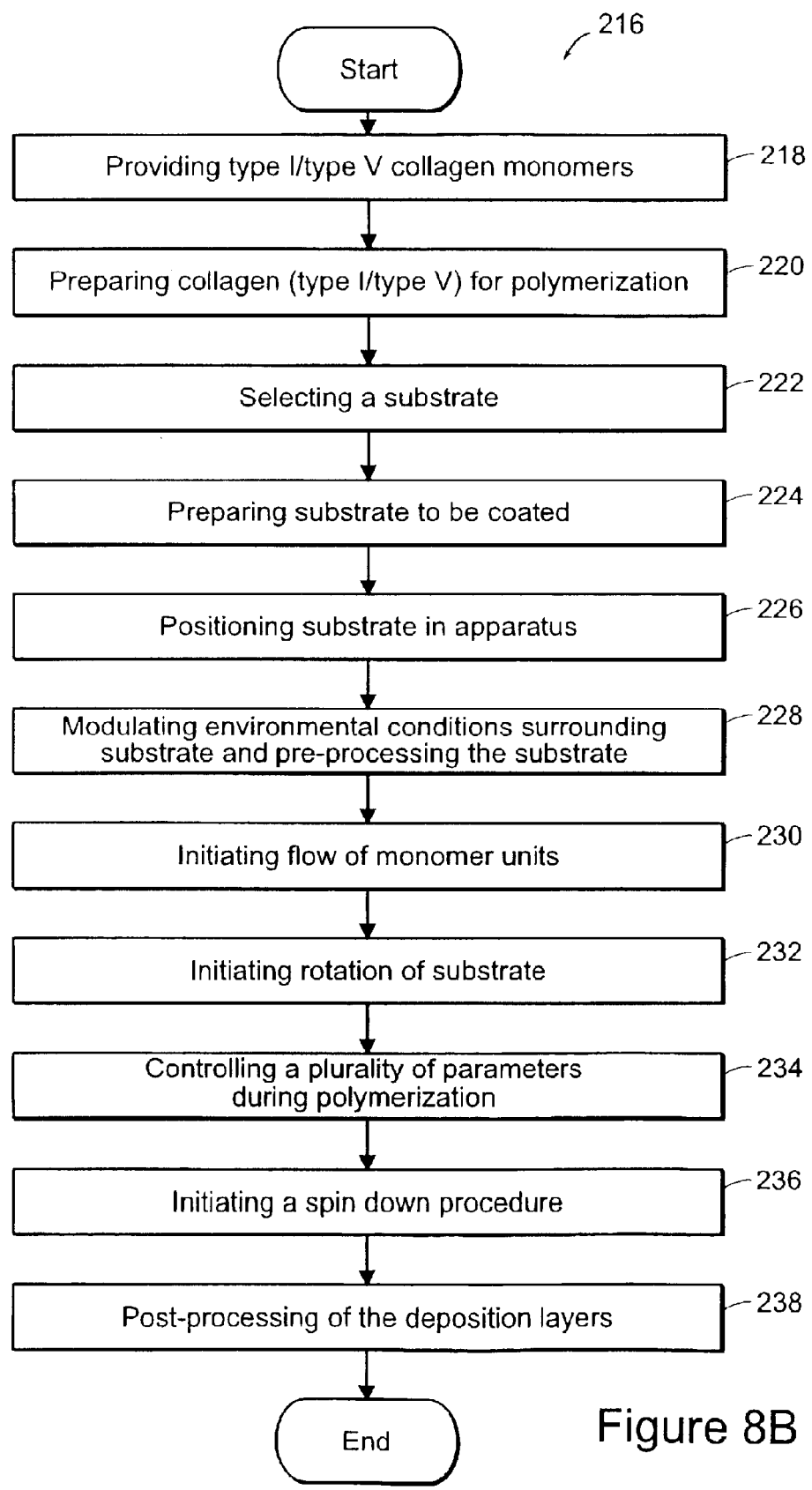
FIG. 8B illustrates a flow chart of a preferred embodiment for producing aligned collagen fibers in accordance with a preferred embodiment of the present invention.

FIG. 8A illustrates an apparatus having an offset holder wherein a monomer solution is deposited onto the substrate at the center of the offset dish holder in accordance with a preferred embodiment of the present invention. FIG. 8B illustrates a preferred methodology to create single and multiple layers of aligned polymer films in accordance with a preferred embodiment of the present invention. In this system and method a substrate is placed off-center on a substrate holder. The holder 206 is rotated at a prescribed velocity or sequence of velocities to create a thin shearing flow. The monomer solution 202 is added to the deposition substrate 210 (either by steady flow or by unsteady dripping) and is carried radially away from the injection point by the centripetal acceleration. Thus a single layer (film) of aligned collagen fibrils is created. To generate multiple layers with different alignment directions, the deposition substrate 210 is rotated at any prescribed angle and another layer may be deposited.

FIG. 8B is a flow chart describing method 216 for generating aligned collagen via spin-coating in accordance with a preferred embodiment of the present invention. The method begins with step 218 of obtaining commercially available type I collagen monomers. They are kept refrigerated at 4–6° C. Extracted or recombinant human and/or animal collagen type I monomers may be used. Collagen type I monomer concentrations are in the range of 0.01 mg/ml to 100 mg/ml with a preferred range of 0.5 to 10 mg/ml. A preferred embodiment utilizes Vitrogen (brand) bovine collagen (3.0 mg/ml). In an alternate embodiment, if heterotypic fibrils are being made for diameter control, type V collagen monomer is obtained as well. Extracted or recombinant human and or animal collagen type V monomers may be used.

Per step 220, collagen type I is prepared for polymerization. In a preferred embodiment, Vitrogen is neutralized in preparation for self-assembly by adding 8:1:1 ratio of collagen type 1:10×PBS: 0.1M NaOH. The pH is adjusted to 7.4. If type V is also included, the solution is further processed to ensure neutralization of type V as well. In preferred embodiments, additives may be used to alter the viscosity of the collagen solution to change the shear stress on the growing fibrils. Such additives include, for example, but are not limited to, glycerol. The viscosity of the final solution of monomer is in the range of 1.0 mPa-s to 100.0 Pa-s. The preferred range is from 5.0 mPa-s to 1.0 Pa-s. In a preferred embodiment, the viscosity of the collagen monomer solution is approximately 10.0 mPa-s The method 216 in accordance with the preferred embodiment includes the step 222 of substrate selection. The substrate that accepts the collagen coating may comprise of any material that can be generated with a uniform optically flat surface to promote the establishment of a uniform shear flow field during spin-coating. Asperities on the surface of the material may be in a range of 0.0 to 10 microns, with a preferred range of 0.1 to 0.5 microns. A preferred embodiment, for example, utilizes a 2 inch diameter borosilicate glass disk.

The method 216 also includes the step 224 of preparation of the substrate to be coated with collagen. Preparation may include modulation of the surface of substrate to be uniformly hydrophilic, uniformly hydrophobic, gradient hydrophilic, or to preferentially bind collagen, for example, antibody inclusion. A preferred embodiment for hydrophilic treatment for glass substrate utilizes, for example, 1.5 hour ultrasonication of substrate in 10% micro90 (brand) cleaner. Glass is stored in deionized water until use.

Per step 222, the substrate to be coated with collagen is positioned into the device designed to generate centripetal acceleration. In a preferred embodiment, the substrate is placed directly onto a vacuum chuck of a commercial spin-coater.

If multiple layers of collagen oriented at differing relative angles are desired another substrate handling system is required, for example, in a preferred embodiment a borosilicate glass disk is placed in an offset disk holder of FIG. 8 or a system as shown in FIG. 4 is utilized.

The method 216 includes the step 228 of modulating the environment surrounding substrate to create conditions conducive to initiate polymerization of collagen. The environmental conditions include a temperature range of 30° C. to 45° C. with a preferred range of 35° C. to 42° C. and 80–100% humidity with a preferred range of 90–100% humidity. In a preferred embodiment, a steam heat humidifier is attached to vent ports in the housing of the substrate rotating device as shown in FIG. 1. In alternate embodiments, the substrate or substrate holder may also incorporate a heating device to locally control temperature of the substrate surface. Such devices require rotating electrical contacts.

A preferred embodiment of the present invention includes pre-processing or pre-wetting the substrate. Prior to sustained addition of the monomer to the substrate, a bolus of cold monomer is added to the substrate to ensure that the substrate is fully wet. In a preferred embodiment, an amount capable of covering the entire substrate is injected and is used to be spread on the substrate.

The method 216 further includes step 230 of initiating a flow of the monomer units. Prior to substrate rotation, a flow of monomer is begun. For neutralized Vitrogen solution the start up range is 0.05–1000 ml/min with a preferred range of 0.1–100.0 ml/min. In a preferred embodiment, the start up flow rate for neutralized Vitrogen solution is 2.0 ml/min.

The method then includes the step 232 of initiating rotation of the substrate. The rotation of substrate is initiated and may proceed in a series of steps to aid in the uniform spreading of the collagen monomer solution over the substrate surface. A range of initial angular velocities during startup is 10 to 5000 rpm with a preferred range of 60 to 1000 rpm. In a preferred embodiment the initial angular velocity utilized is 250 rpm.

The method further includes the step 234 of controlling a plurality of parameters during polymerization. For example, the rotational velocity of the substrate during polymerization is set. During the polymerization of the collagen monomer on the warm substrate, the rotational velocity may remain steady or undergo modulation of any kind. However, the average velocity (based on averaging over each minute of operation) of the substrate has a range of 100 to 50,000 rpm with a preferred range of 500 to 10,000 rpm. In a preferred embodiment, the average rotational velocity of the substrate is 1600 rpm.

Further, during polymerization, the flow rate of monomer is controlled. The monomer solution flow rate provides a monomer for polymerization to the substrate surface while generating suitable shear force under rotation to induce alignment of the growing collagen fibrils. The flow rate of collagen solution over the rotating substrate may remain steady or undergo modulation of any kind. However, the average flow rate of collagen solution (based on averaging over each minute during operation) is in a range of between 0.05 ml/min to 1000 ml/min with a preferred range of 0.1 to 100 ml/min. In a preferred embodiment, the average flow rate over the substrate during polymerization is 0.25 to 2.0 ml/min.

Another parameter that is controlled during polymerization is the optimum shear rate at the substrate interface. The flow rate over the growing monomers tends to align them along the flow direction and provides the monomer units to the free end. The combination of monomer solution input flow rate, viscosity and substrate rotational velocity combines to produce a range of shear rates from 1.0 to 500,000 Hz with a preferred range of 50 to 50,000 Hz. In a preferred embodiment, the shear rate at the substrate surface is approximately 700 Hz.

The duration of polymerization is another parameter that can be controlled. Rheological experiments have demonstrated that the gelation of the collagen solution begins once optimum conditions are achieved and take approximately six minutes following addition to a substrate warmed to 37° C. In the apparatus in accordance with a preferred embodiment of the present invention, the range of time of exposure of the monomer flow to the rotating substrate lies between 1 minute and 2 hours with a preferred range of 3 minutes to 1 hour. In a preferred embodiment, to generate a single layer of polymerized collagen, flow is sustained over the rotating substrate for 15 to 20 minutes.

In preferred embodiments, a layer including collagen type IV and cell adhesion proteins such as, for example, but not limited to, laminin, fibronectin and/or any integrin receptor is deposited between aligned polymer layers.

The method 216 in accordance with the present invention includes the step 236 of initiating a spin-down procedure. Following the addition of collagen to the rotating substrate, the rotating substrate continues spinning to remove excess collagen monomer. This spinning down procedure may include a rinse step where a solution containing no collagen monomer is applied to the rotating substrate to enhance the removal of unreacted monomer or to add a layer of material to separate collagen layers, for example, to promote cell attachment and proliferation. Such materials may include proteoglycans, laminin, fibronectin and/or vinculin or integrin moieties. During the spin-down procedure the rotational velocity may remain steady or undergo modulation of any kind. However, the average velocity (based on averaging over each minute of operation) of the substrate is in a range of 100 to 50,000 rpm with a preferred range of 500 to 10,000 rpm. In a preferred embodiment, the average rotational velocity of the substrate is 1600 rpm.

The method 216 concludes with a post-processing step 238. To ensure polymerization of the deposited layer, the substrate may be post-processed. Post-processing may include an extended exposure to the warm humid environment for a period of 0.1 to 60 minutes with a preferred range of exposure of 3 to 10 minutes. In a preferred embodiment, the exposure time during post-processing is 5 minutes. The method 216 includes all of the essential steps to produce a single layer of aligned collagen via spin-coating in accordance with a preferred embodiment of the present invention.

Figure 9:
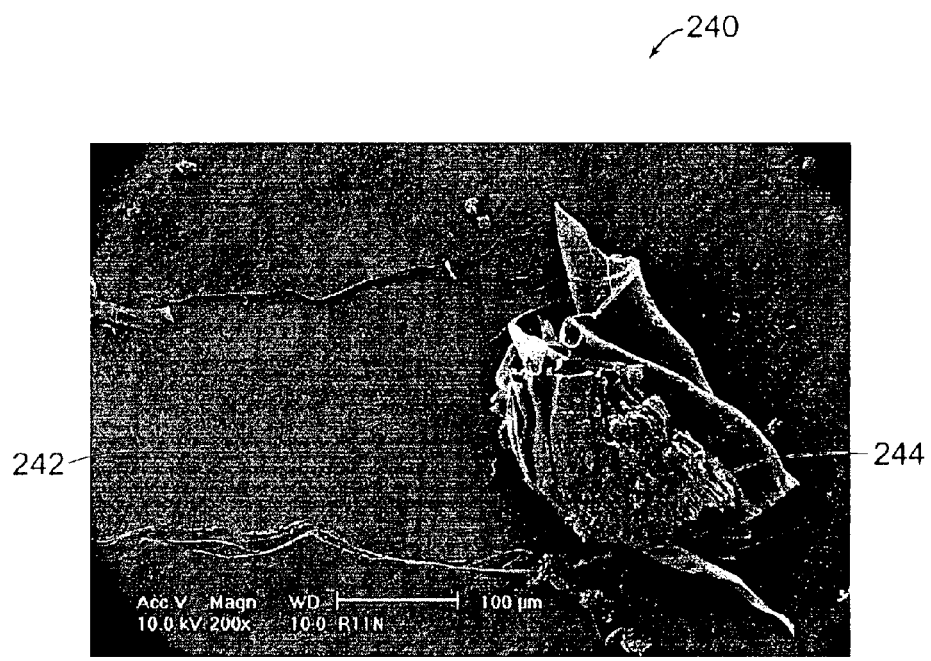
FIG. 9 is a scanning electron microscope (SEM) image demonstrating the deposition of a plurality of thin aligned layers onto a glass substrate in accordance with a preferred embodiment of the present invention.

FIG. 9 is a scanning electron microscope (SEM) image demonstrating the deposition of a plurality of thin aligned layers 244 onto a glass substrate 242 in accordance with a preferred embodiment of the present invention.

Figure 10:
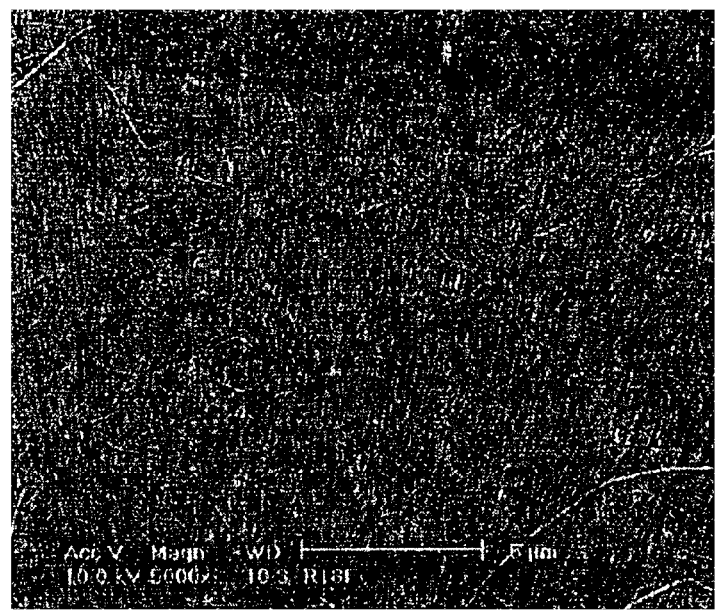
FIG. 10 is a scanning electron microscope (SEM) image of a single layer of predominately aligned collagen fibrils in accordance with a preferred embodiment of the present invention.

FIG. 10 is a scanning electron microscope (SEM) image of a single layer of predominately aligned collagen fibrils in accordance with a preferred embodiment of the present invention.

Figure 11:
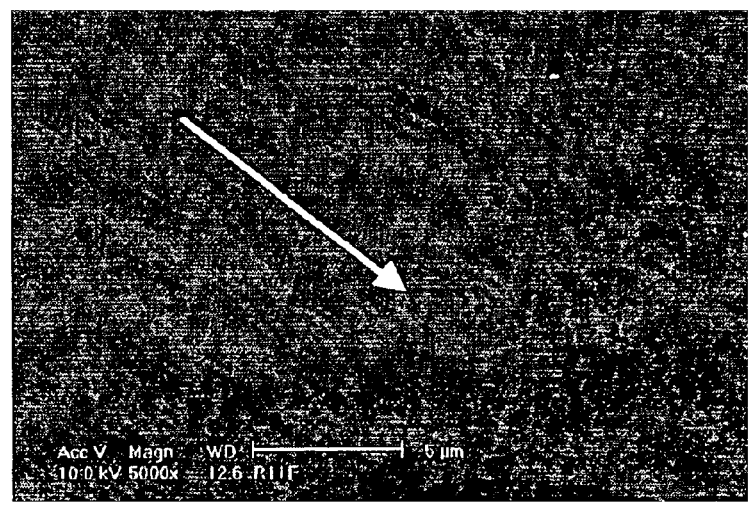
FIG. 11 is a scanning electron microscope (SEM) image of aligned collagen fibrils generated by the spin-coating methodology in accordance with a preferred embodiment of the present invention.

FIG. 11 is a scanning electron microscope (SEM) image of aligned collagen fibrils generated by the spin-coating methodology in accordance with a preferred embodiment of the present invention.

Figure 12:
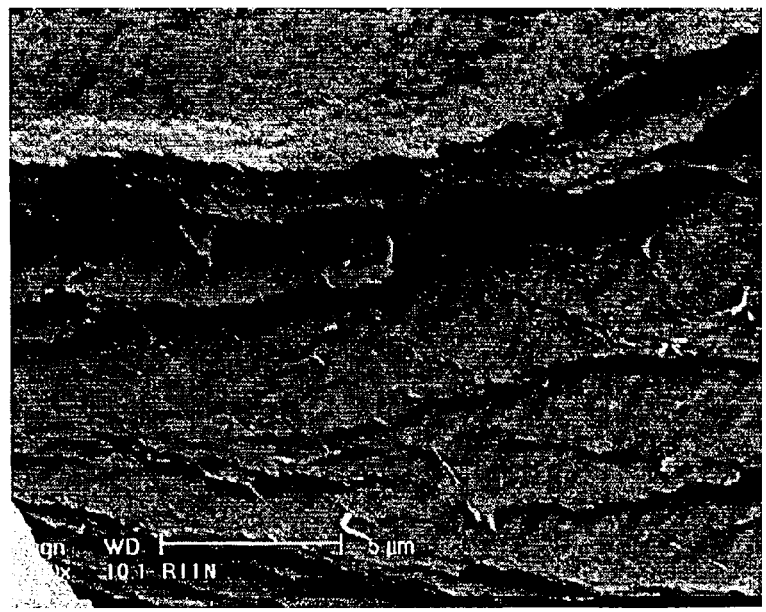
FIG. 12 illustrates a scanning electron microscope (SEM) image demonstrating layering of collagen in pseudolamellae in accordance with a preferred embodiment of the present invention.

FIG. 12 illustrates a scanning electron microscope (SEM) image demonstrating layering of collagen in pseudolamellae in accordance with a preferred embodiment of the present invention. Multiple layers of aligned collagen polymer may be achieved by repeating (indefinitely) the procedure for generating a single layer. The method 216 may be repeated immediately following the post-processing step or repeated following a dryout period or a deionized water soak period. In a preferred embodiment, multiple layers are achieved by repeating the single layer procedure following a 24 hour soaking period in deionized water.

Figure 13:
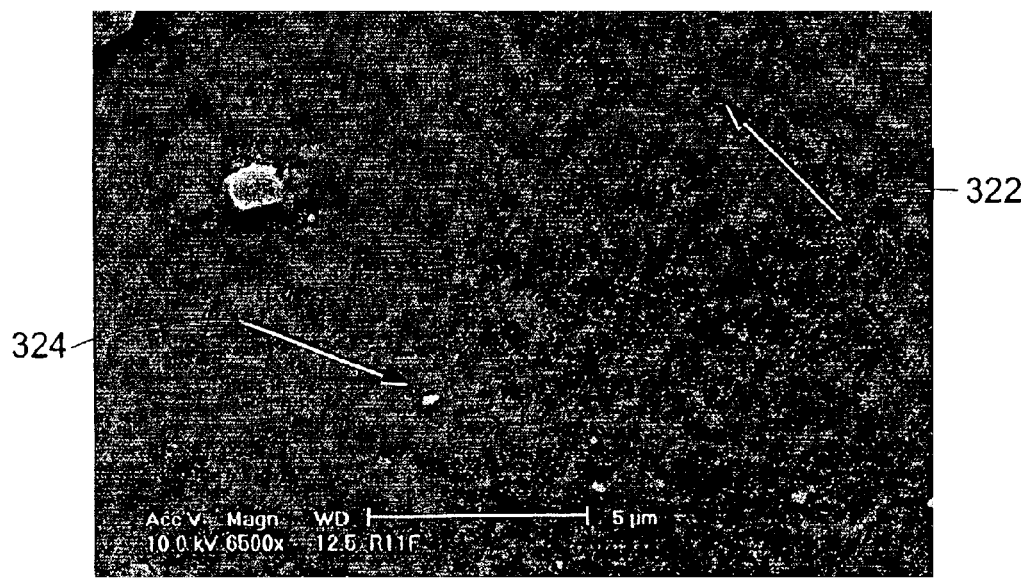
FIG. 13 is a scanning electron microscope (SEM) image illustrating the interaction of two individual layers of aligned collagen in accordance with a preferred embodiment of the present invention.

FIG. 13 is a SEM image 320 illustrating the intersection of two individual layers of aligned collagen in accordance with a preferred embodiment of the present invention. The arrows 322, 324 indicate the alignment directions for each layer. To generate multiple layers of aligned collagen polymer where the relative angle of alignment of the collagen is changed between depositions, the method 216 for producing multiple layers is performed. However, the substrate is rotated through any angle relative to its previous position on the substrate holder. Any range of angles is possible from a range of 0 to $2\pi$ (and any integer multiple thereof) with a preferred range of 0 to $\pi$. In a preferred embodiment, the angle between aligned collagen layers is $\pi/2$.

With regard to microfluidics methodologies, the fundamental principle in the embodiments of the present invention is to use flow regimes to control the growth of individual fibers of collagen, or some other polymerizable material. The method 216 outlined the use of a common industrial process, namely spin-coating, to provide the necessary constraints to the growing fibers to allow control of alignment, length and diameter. However in a more general embodiment it is possible to directly manipulate the flow field, and thus the local environment, around a growing filament. To this end the use of the emerging field of microfluidics can be used.

The use of microfabricated fluid handling is described by Giordano, N. and Cheng, J.-T. (2001) in the Journal of Physics: Condensed Matter, 13, R271–R295 entitled "Microfluid mechanics: progress and opportunities", the entire teachings of which is hereby incorporated by reference. These methods have matured over the last few years resulting in commercial products such as DNA sorting systems. These systems can be used to handle fluids on sub-micron scales using features and channels that can be applied to sub-micron dimensions.

To control single growing filaments, the length scales required must be closer to the characteristic dimension of the filament, approximately 50 nm. Confinement in tubes rapidly allows extension of the filament and the narrow confines of such a channel rapidly increase the shear rates around the filament. However these narrow channel sizes are currently difficult to manufacture and use. A solution is described by a preferred embodiment of the present invention and uses a form of flow focussing illustrated in FIGS. 14A–14C which provide a schematic of the flow focussing concept. At the length scales discussed herein flow is almost always laminar. This means that in fact mixing is very difficult to encourage in such flow regimes. In reality then the mixing process is controlled by diffusion processes. Consequently if two jets impinge on each other at an angle they do not mix directly but must mix by diffusion across the interface. If one of these jets contains the un-polymerized collagen (or other species) discussed hereinbefore, and the other jet contains the polymerizing agent then there is a finite time before enough diffusion occurs to allow mixing.

If the polymerizing jet has a higher volume flow rate and both jets enter the same size channel, then the amount of the channel used by each fluid "species" is proportional to the incoming flow rate. Consequently this behavior allows the fluids to control the active zone in the flow field, both through constriction of the width as shown in FIG. 14B, related to the relative flow rates (this is the flow focusing described hereinbefore), and through diffusion related to fluid concentrations.

The procedure outlined with respect to FIGS. 14A–14C allow a confined area to be generated in a flow field that can be arranged to have the correct solution conditions for polymerization. In addition other fluids can be added to influence the filament diameter and, if necessary, stop polymerization. If the growing polymer is advanced such that the growing tip is always in this critical region, the polymer can be extruded indefinitely. This approach allows the nanofabrication of a single polymer.

Figure 15:
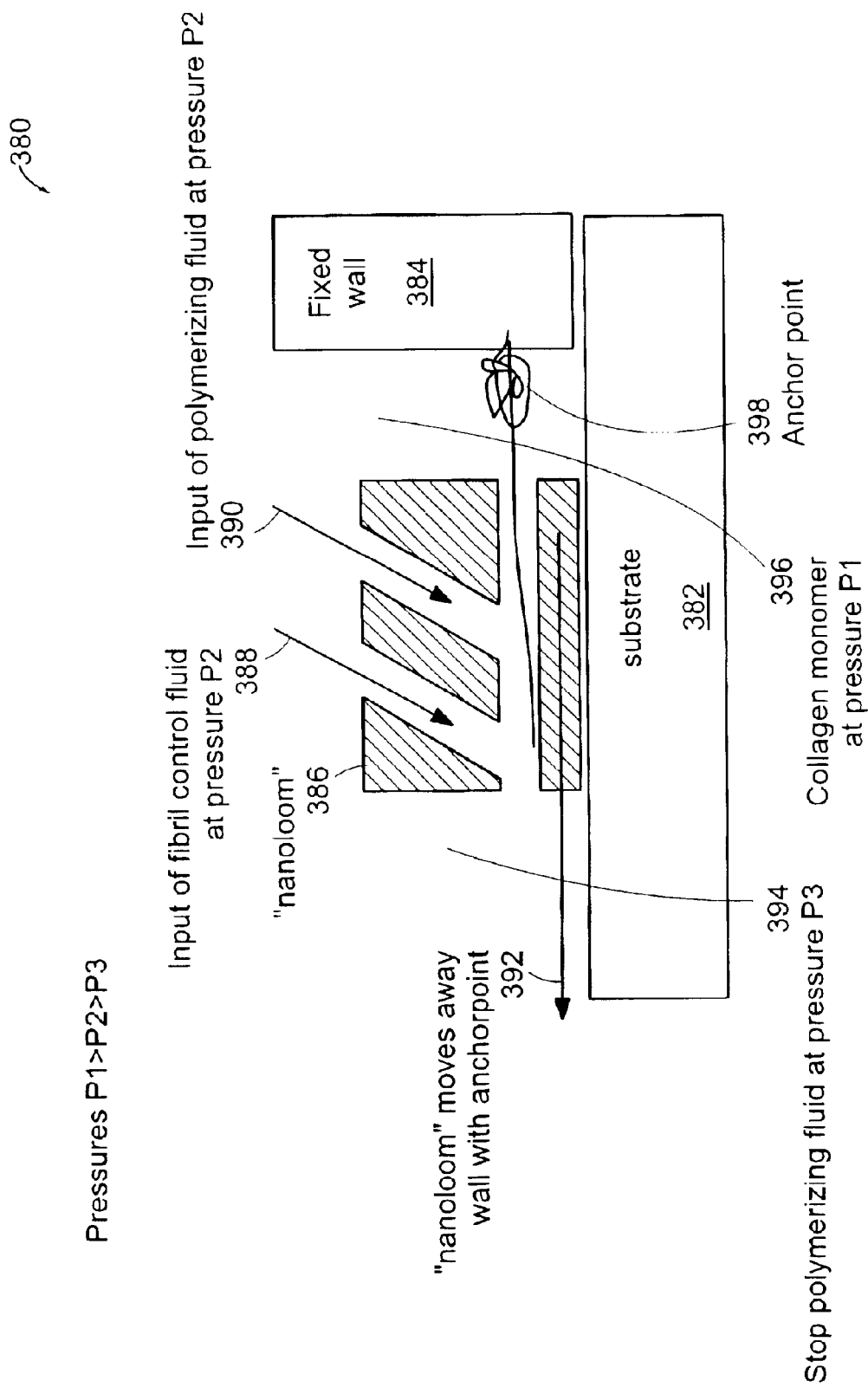
FIG. 15 schematically illustrates another preferred system to manufacture layered, aligned polymer structures in accordance with a preferred embodiment of the present invention.

FIG. 15 illustrates another preferred system to manufacture layered aligned polymer structures in accordance with a preferred embodiment of the present invention. This preferred embodiment utilizes the recognition that if an array of channels such as described in FIGS. 14A–14C is manufactured an array of controlled polymers can be generated. In FIG. 15, initially the collagen is polymerized against a fixed wall 384 to ensure a dangling collagen chain is present in the nanoloom 386. As the collagen filament grows this nanoloom 386 advances relative to the fixed wall, thus extruding a single collagen filament as it advances. An array of these filaments allow construction of a single layer of aligned collagen. It may also be possible to produce woven materials in this manner.

Figure 16A:
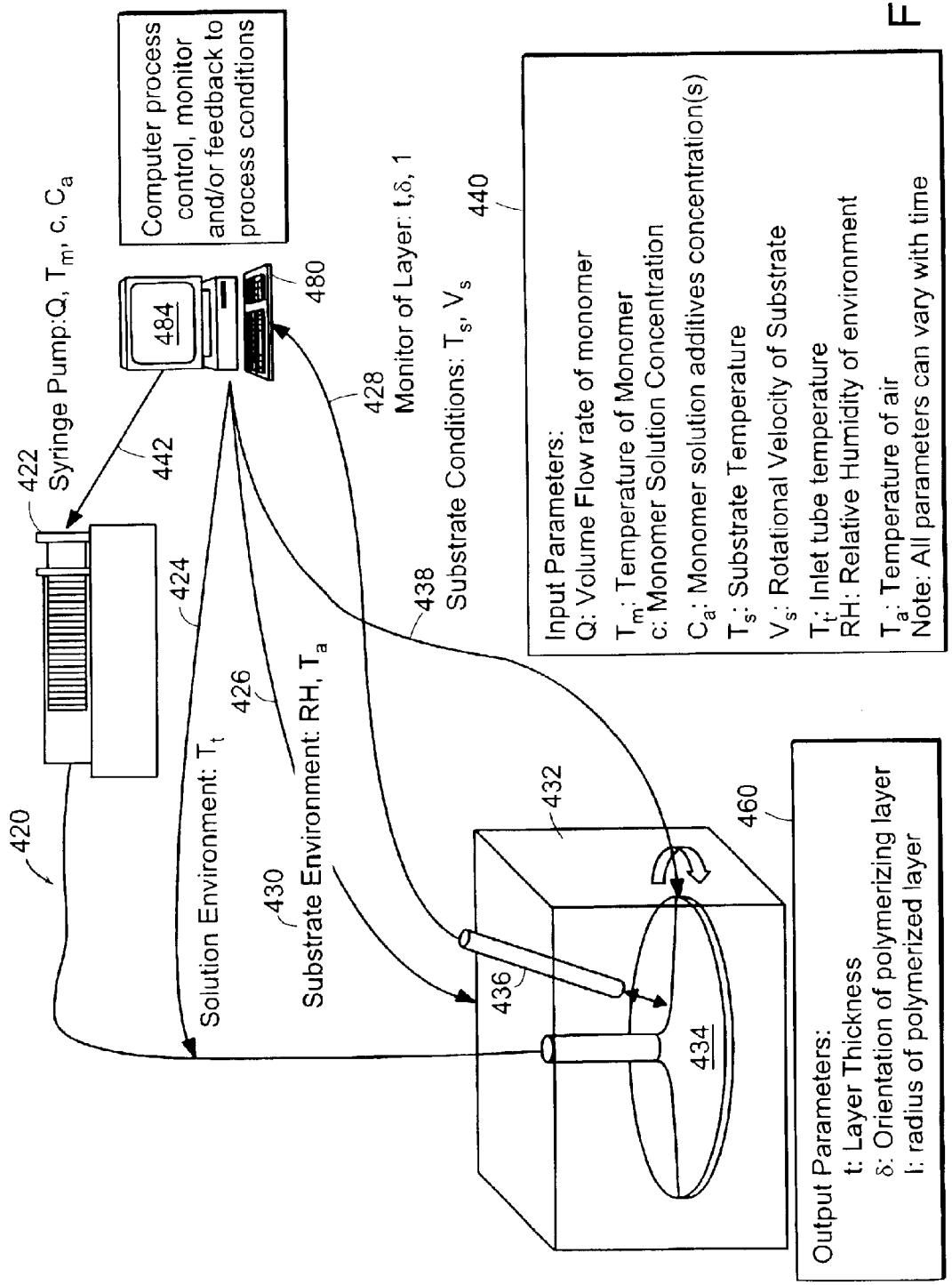
FIGS. 16A and 16B illustrate a block diagram and a schematic diagram, respectively, of a preferred embodiment system to manufacture layered, aligned polymer structures in accordance with a preferred embodiment of the present invention.
Figure 16B:
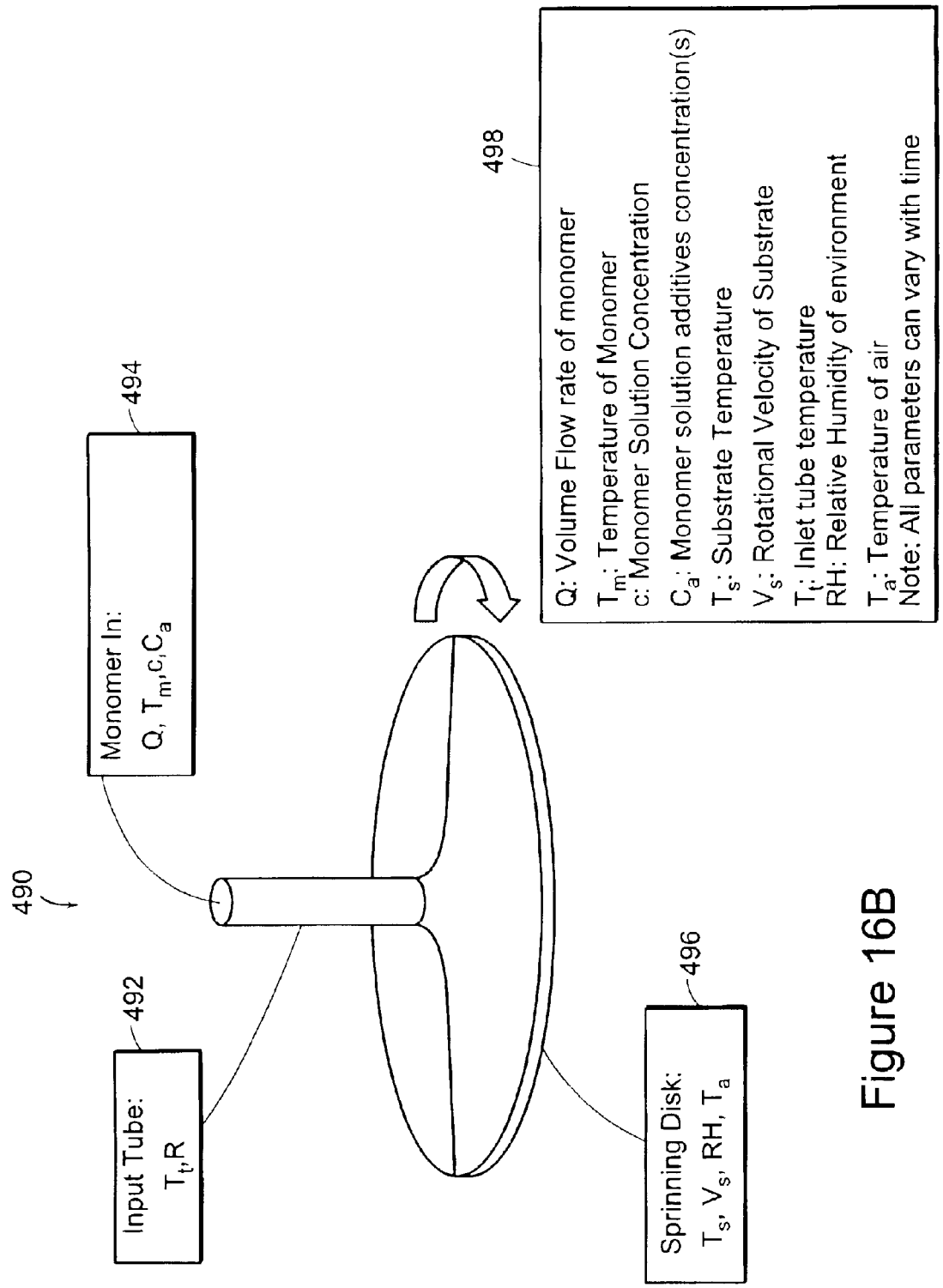

FIGS. 16A and 16B illustrate a block diagram 420 and a schematic diagram 490, respectively, of a preferred embodiment system to manufacture layered, aligned polymer structures in accordance with the present invention. The apparatus 432 used to generate layered, aligned polymer structures has a plurality of input parameters 440 that can be modulated using a processor 480. The input parameters, include, without limitation, volume flow rate of monomer, temperature of monomer, monomer solution concentration, concentrations of monomer solution additives, substrate temperature, rotational velocity of substrate, inlet tube temperature, relative humidity of environment, and temperature of air. It should be noted that all parameters can vary with time. A plurality of output parameters 460 are also monitored and modulated by the processor 480. The output parameters include, without limitation, layer thickness, orientation of polymerizing layer, and radius of polymerized layer. The system includes a plurality of sensing elements and monitoring elements that enables the processor 480 to process, control and monitor different parameters. The processor through an input/output interface 442 interfaces with a pump to monitor and/or control the volume flow rate of the monomer, the temperature of the monomer, the concentration of the monomer solution and the concentration of any additives to the solution. Further, the solution environment, for example, the temperature of the solution is monitored using the interface 424. The substrate environment, for example, the relative humidity and the temperature can be monitored and modulated using an interface 426. The substrate conditions are monitored such as, for example, substrate temperature and the rotational velocity of the substrate. The parameters associated with the layers of aligned polymers, for example, layer thickness, orientation of polymerizing and radius of polymerized layers are also monitored using an interface 428. The processor 480 can have an integrated display device or provide data to another display device and/or processor that is not co-located with the apparatus 432. Post-processing of the polymer structure as described with respect to the method illustrated in FIG. 8B can be controlled by the processor 480. It should be noted that the device 432 can comprise a distribution network for the polymer solution that includes a plurality of nozzles that can be rotated and deposit the polymer/monomer solution onto a substrate that can be stationary. The shear flow is generated by a relative motion and/or velocity between the distribution system and the substrate.

The system 420 may also include a microprocessor and a memory device that stores display data. The microprocessor may include an operating system, as well as application and communication software to implement the functions with respect to controlling device 432 operation. The operating system for the system of the present invention includes a processing system with at least one high speed processing unit and a memory system. In accordance with the practice of persons skilled in the art of computer programming, the present invention has been described herein with reference to acts and symbolic representations of operations or instructions that are performed by the processing system. Such acts, operations and instructions are also referred to sometimes as being computer executed or processing unit executed.

It will be appreciated that the acts and symbolically represented operations or instructions include the manipulation of electrical signals by the processing unit. An electrical system with data bits causes a resulting transformation or reduction of the electrical signal representation, and the maintenance of data bits at a memory location in the memory system to thereby reconfigure or otherwise alter the processing unit's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic disks, and any other volatile or non-volatile mass storage system readable by the processing unit. The computer readable medium includes cooperating or interconnected computer readable media, which exist exclusively on the processing system or is distributed among multiple interconnected processing systems that may be local or remote to the processing system.

It should be understood that the programs, processes, methods and systems described herein are not related or limited to any particular type of computer or network system (hardware or software), unless indicated otherwise. Various types of general purpose or specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams. While various elements of the preferred embodiments have been described as being implemented in software, other embodiments in hardware or firmware implementations may alternatively be used, and vice-versa.

It will be apparent to those of ordinary skill in the art that methods involved in layered aligned polymer structures and methods of making same may be embodied in a computer program product that includes a computer usable medium. For example, such a computer usable medium can include a readable memory device, such as, a hard drive device, a CD-ROM, a DVD-ROM, or a computer diskette, having computer readable program code segments stored thereon. The computer readable medium can also include a communications or transmission medium, such as, a bus or a communications link, either optical, wired, or wireless having program code segments carried thereon as digital or analog data signals.

The systems and methods of the present invention can be used in a plurality of applications. For example, single layers of aligned collagen can be manufactured which can be used as a test bed for assessing effects of aligned collagen matrices on cellular behavior in connective tissue fibroblasts, in epithelia and in endothelia. Further they can generate scaffolding to promote adhesion and proliferation of cell populations in corneal epithelium and/or corneal endothelium.

Further, these embodiments of the present invention can be used to generate multiple layers of aligned collagen which can be used as a test bed for examination of the behavior of cells in anisotropic extracellular matrix including cartilage fibroblasts, corneal keratocytes, and tendon fibroblasts. They can generate connective tissue scaffolding for repair and promotion of cellular adhesion and proliferation that can be used in, for example, but not limited to, artificial corneal replacement, corneal repair material, transfer scaffolding for epithelial transplants, transfer scaffolding for endothelial transplants, tendon replacement or repair, ligament replacement or repair and annulus fibrosis replacement or repair. In addition, biocompatible strengtheners for natural and/or artificial materials for use in tissue repair or replacement can be generated using the embodiments of the present invention. These can be rolled up to perform annulus fibrosis function while embedded in a poly(vinyl alcohol) matrix, or be used as strengtheners for corneas made from artificial materials, for example, poly HEMA and/or be a resorbable anchor for tissue repair.

Further applications of the preferred embodiments include generating multiple layers of other aligned biopolymers that can be used as biocompatible scaffolding, for example, "braids" to strengthen stents, or other implants. They can also be used as guidance for nerves, for example, nerve cuffs. Other applications having layers where alignment is not important that can benefit from the layered polymer structures of the present invention include support for species embedded in multiple layers such as cells and drug release applications.

In addition, applications that include non-biopolymers may benefit from the deposition of layered, aligned polymer structures, for example, generation of optical storage media.

The claims should not be read as limited to the described order or elements unless stated to that effect. Therefore, all embodiments that come within the scope and spirit of the following claims and equivalents thereto are claimed as the invention.

What is claimed:

1. A method of producing a thin layer of oriented polymer structures, comprising the steps of:

controlling the flow of a predominantly monpmeric solution of self-assembling subunits into a device having a substrate, the device generating a shear flow;

inducing polymerization by self-assembly of the subunits while in the shear flow;

controlling at least one solution parameter and at least one environment parameter during polymerization, wherein the solution parameters are solution temperature, solution viscosity, solution flow rate, subunit concentration and the environment parameters are local air temperature during polymerization and local relative humidity during polymerization; and generating a layer of oriented polymer structures.

2. A method of producing a thin layer of oriented polymer structures, comprising the steps of:

controlling the flow of a predominantly monomeric solution of self-assembling subunits into a device having a substrate, the device generating a shear flow;

inducing polymerization by self-assembly of the subunits while in the shear flow;

controlling at least one of the parameters of solution temperature, solution viscosity, solution flow rate, subunit concentration, local air temperature during polymerization and local relative humidity during polymerization; and generating a layer of oriented polymer structures, wherein the polymer is collagen and the oriented polymer structures are fibrils.

3. The method of claim 2, wherein the method further comprises the steps of:

mixing a solution of collagen with phosphate buffered saline solution;

adjusting the pH of the solution to 7.4±0.2;

applying the solution at a controlled rate onto a substrate to generate a shearing flow;

causing preferential orientation of the forming collagen fibrils; and repeating the process to generate successive layers.

4. The method of claim 3, wherein the layers have a uniform controlled thickness ranging from sub-micron to 100 microns.

5. The method of claim 2, wherein the collagen is either type I collagen or type V collagen.

6. The method of claim 3, wherein the principle orientation of the aligned fibrils in a single layer alternates in each successive layer.

7. The method of claim 3, wherein the angle between the principle orientation of each layer is approximately in the range of 0 to 180 degrees.

8. The method of claim 1, wherein solution temperature, and subunit concentration are controlled and further comprising the step of controlling the surfactant composition of the solution.

9. The method of claim 1, wherein the shear flow is generated by spinning the substrate at a controlled rate in a range of approximately 50 to 50,000 Hz.

10. The method of claim 2, wherein the shear flow is generated by drawing the substrate out of the solution.

11. The method of claim 1, wherein the atmosphere is controlled to a specified temperature and relative humidity.

12. The method of claim 1, wherein the solution conditions are modulated to control the polymerization kinetics and morphology.

13. The method of claim 1, wherein the use of shear flow aligns polymerizing polymer chains in a layer such that polymers are predominantly aligned parallel to each other.

14. The method of claim 1, further comprising angular rotation of the substrate providing shear flow and confinement to orient the polymerized polymers.

15. The method of claim 14, wherein an input flow rate, solution viscosity and substrate rotational velocity combine to produce a shear rate between 1 $s^{-1}$ and 500,000 $s^{-1}$.

16. The method of claim 14, wherein an input flow rate, solution viscosity and substrate rotational velocity combine to produce a shear rate of 10 $s^{-1}$ to 10,000 $s^{-1}$.

17. The method of claim 2, wherein a second oriented polymer layer is produced on top of a first polymer layer by repeating the method.

18. The method of claim 17, wherein a rotating surface is displaced laterally with respect to the flow of the predominantly monomeric solution to change a deposition direction on the substrate.

19. The method of claim 17, wherein the second layer comprises a different material than the first layer.

20. The method of claim 17, wherein the second layer is a promoter of at least one of cell adhesion and proliferation.

21. The method of claim 17, wherein an additional layer comprising a protein selected from the group consisting of collagen type IV, laminin, fibronectin, an integrin receptor and a mixture thereof is deposited before the second oriented polymer layer is produced.

22. The method of claim 17, wherein a construct comprising a plurality of oriented polymer layers is used as a replacement or repair of the human stroma.

23. The method of claim 17, wherein the orientation of the polymers in a plane of a layer in the second and subsequent layers is predominantly orthogonal with the alignment of the polymers in the plane of a layer in the first layers.

24. The method of claim 2, wherein the predominantly monomeric solution is an aqueous solution.

25. The method of claim 24, wherein the solution is an aqueous collagen solution.

26. The method of claim 24, wherein the solution comprises extracted collagen or recombinant collagen.

27. The method of claim 25, wherein the collagen is Type I collagen.

28. The method of claim 25, wherein the collagen is a mixture of Type I collagen and Type V collagen.

29. The method of claim 1, wherein the flow is at a constant rate.

30. The method of claim 1, wherein the flow rate is between 0.05–1000 ml/min.

31. The method of claim 1, wherein the flow rate is between of 0.1–100.0 ml/min.

32. The method of claim 1, further comprising the step of spinning off any excess solution from the substrate.

33. The method of claim 1, further comprising the substrate and a substrate holder being modified to minimize waste of solution.

34. The method of claim 2, wherein the solution is composed of 8:1:1 ratio of collagen type I (3 mg/ml) to 10× phosphate buffered saline to 0.1M NaOH with pH adjusted to 7.4.

35. The method of claim 1, wherein the viscosity of the solution is between 1 mPa.s and 100 Pa.s.

36. The method of claim 1, where the viscosity of the solution is between 5 mPa.s and 1 Pa.s.

37. The method of claim 2, wherein the substrate comprises one of a flat surface or curved surface.

38. The method of claim 37, wherein the flat surface is optically smooth.

39. The method of claim 37, wherein the flat surface has a surface roughness of less than approximately 10 micrometers.

40. The method of claim 37, wherein the substrate is a borosilicate glass disk.

41. The method of claim 1, wherein a surface of the substrate is treated to control adhesion of the polymer and wetting of the solution.

42. The method of claim 41 wherein the surface of the substrate is treated with a detergent.

43. The method of claim 41 wherein a surface of the substrate is plasma cleaned.

44. The method of claim 41 wherein the substrate has a surface treatment that is heterogeneous.

45. The method of claim 41 wherein the substrate has a surface treatment that is patterned.

46. The method of claim 45 wherein the pattern of the surface treatment constrains the flow.

47. The method of claim 2 wherein the air temperature range is controlled in the range of 30° C.–45° C. and relative humidity is controlled in the range of 80–100%.

48. The method of claim 2 wherein the air temperature range is controlled in the range of 35° C.–42° C. and relative humidity is controlled in the range of 90–100%.

49. The method of claim 1, wherein the rotation velocity of the substrate is used to control layer thickness and final morphology of the oriented polymer structures.

50. The method of claim 49, wherein the layer thickness is between 100 nm and 1 mm.

51. The method of claim 49, wherein the layer thickness ranges between 0.5 μm and 100 μm.

52. The method of claim 49, wherein the substrate rotational velocity is varied.

53. The method of claim 49, wherein the velocity is initially between 10 to 5,000 rpm.

54. The method of claim 49, wherein the velocity is initially between 60 to 1,000 rpm.

55. The method of claim 49, wherein the velocity during polymerization is constant.

56. The method of claim 49, wherein the velocity during polymerization is varied.

57. The method of claim 49, wherein the velocity is in the range 100 to 50,000 rpm.

58. The method of claim 49, wherein the velocity ranges from 500 to 10,000 rpm.

59. The method of claim 49, wherein the average velocity is in the range 100 to 50,000 rpm.

60. The method of claim 59, wherein the average velocity ranges from 500 to 10,000 rpm.

61. The method of claim 2, wherein the solution further includes at least one additive to control the polymerization process and final morphology of the layer.

62. The method of claim 61, wherein an additive is a proteoglycan.

63. The method of claim 61, wherein an additive is selected from the group consisting of chondroitin sulfate, dermatan sulfate, a keratan sulfate proteoglycan and mixtures thereof.

64. The method of claim 62, wherein the proteoglycan is selected from the group consisting of decorin, lumican, biglycan, keratocan, syndican and a mixture thereof.

65. The method of claim 62, wherein the percent (by weight) of proteoglycan is between 0.25 and 50.0.

66. The method of claim 62 wherein between 0.5 and 10 weight percent of a proteoglycan is added to the solution.

67. The method of claim 2 wherein the substrate has at least one channel and at least one polymerization channel is used to guide the growth of the polymer structure.

68. The method of claim 67 wherein the growing polymer structure is attached to a fixed point and is extruded from the polymerization channel during polymerization.

69. The method of claim 67, wherein the growing polymer structure is attached to a moving plate pulled through the polymerization channel where conditions conducive to polymerization are maintained.

70. The method of claim 67, wherein conditions outside the polymerization channel are not conducive to polymerization.

71. The method of claim 67, wherein said polymerization channel is part of an array of identical channels.

72. The method of claim 67 wherein said polymerization channel is treated to prevent adhesion of polymerizing material.

73. The method of claim 67, wherein said polymerization channel is obtained from a self-assembled three dimensional network.

* * * * *